United States Patent [19]
Battiato et al.

[11] Patent Number: 5,925,022
[45] Date of Patent: Jul. 20, 1999

[54] MEDICAL FLUID INJECTOR

[75] Inventors: Dane J. Battiato, Cincinnati, Ohio; Gary S. Wagner, Taylor Mill, Ky.; Steve P. Verdino, Cincinnati; Robert G. Bergen, Westchester, both of Ohio; James E. Knipfer, Ft. Wright, Ky.; Pamela K. Jacobs; Peter F. Staats, both of Loveland, Ohio; John N. Minnich, Lockland, Ohio; Charles S. Neer, Milford, Ohio; James H. Goethel, Cincinnati, Ohio

[73] Assignee: Liebel-Flarsheim Company, Cincinnati, Ohio

[21] Appl. No.: 09/189,337

[22] Filed: Nov. 10, 1998

Related U.S. Application Data

[62] Division of application No. 08/753,288, Nov. 22, 1996, Pat. No. 5,868,710.

[51] Int. Cl.$^6$ ........................................ A61M 5/00
[52] U.S. Cl. ........................ 604/208; 604/131; 604/154; 128/DIG. 1
[58] Field of Search ................................. 604/154, 155, 604/65–67, 73, 151, 152, 131, 123, 186, 207–211, 224, 227; 128/DIG. 1, DIG. 13

[56] References Cited

U.S. PATENT DOCUMENTS

| | | | |
|---|---|---|---|
| Re. 35,249 | 5/1996 | Sealfon | 604/135 |
| 2,491,978 | 12/1949 | Helfman et al. | 604/154 |
| 4,804,368 | 2/1989 | Skakoon et al. | 604/155 |
| 5,034,004 | 7/1991 | Crankshaw | 604/154 |
| 5,232,449 | 8/1993 | Stern et al. | 604/154 |
| 5,259,732 | 11/1993 | Stern | 604/154 |
| 5,261,884 | 11/1993 | Stern et al. | 604/154 |
| 5,295,966 | 3/1994 | Stern et al. | 604/154 |
| 5,451,211 | 9/1995 | Neer et al. | 604/218 |
| 5,658,261 | 8/1997 | Neer et al. | 604/154 |
| 5,695,464 | 12/1997 | Viallet | 604/131 |
| 5,807,340 | 9/1998 | Pokras | 604/183 |

Primary Examiner—Wynn Wood Coggins
Assistant Examiner—Sharon Finkel
Attorney, Agent, or Firm—Wood, Herron & Evans, L.L.P.

[57] ABSTRACT

A medical fluid injector includes: an air detection system for detecting air in the neck of the syringe; a hand-operated control lever for controlling movement of the injector ram; magnetic conductors for delivering magnetic fields from a power head face plate to an internal circuit board to permit detection of different face plates; a tilt sensor detecting the tilt angle of the power head to control the speed of motion brought about by the hand-operated control lever and to control an invertible display; and a monitor microcontroller for monitoring the behavior of the central processing unit to detect and react to error conditions.

11 Claims, 13 Drawing Sheets

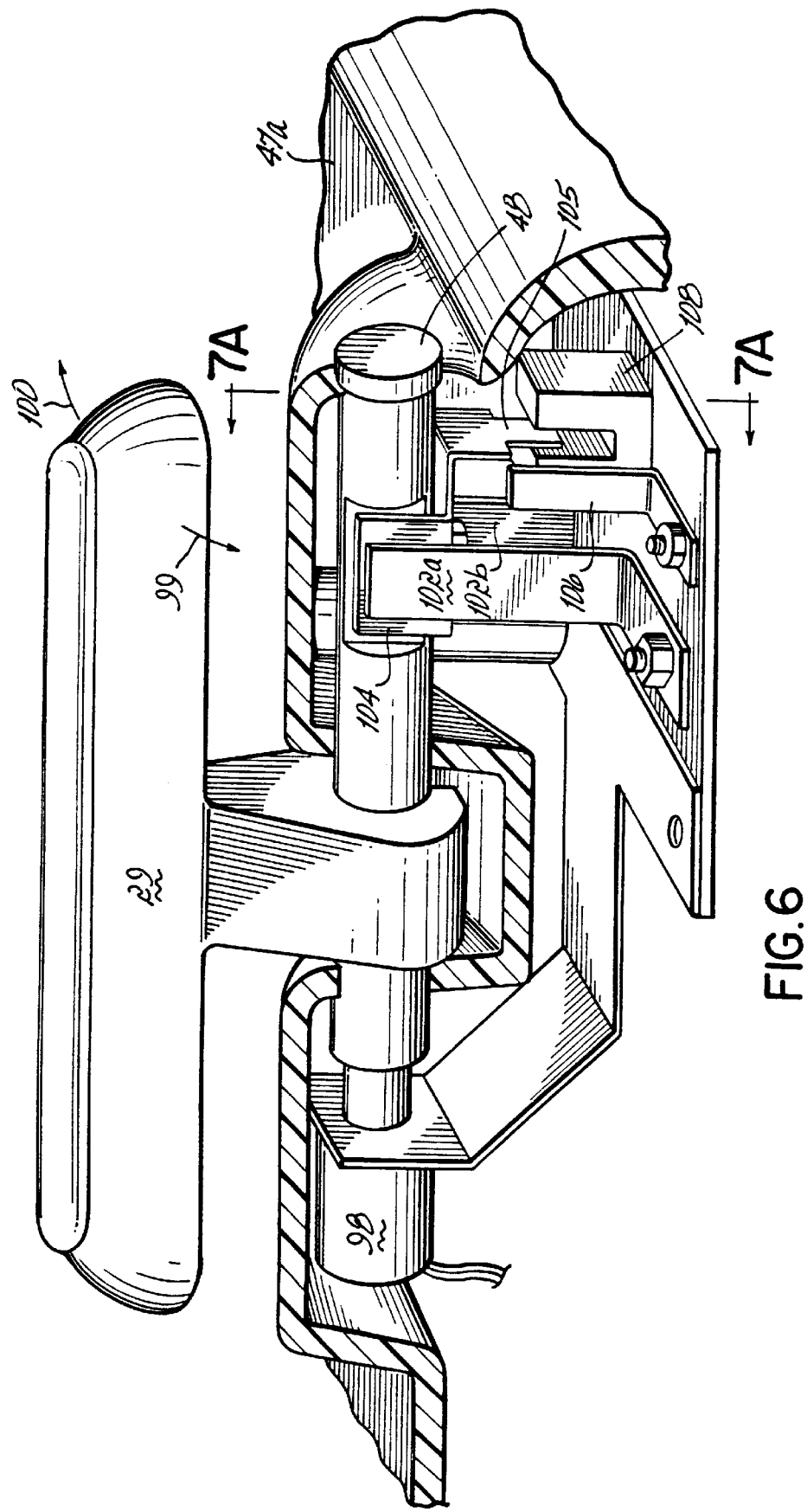

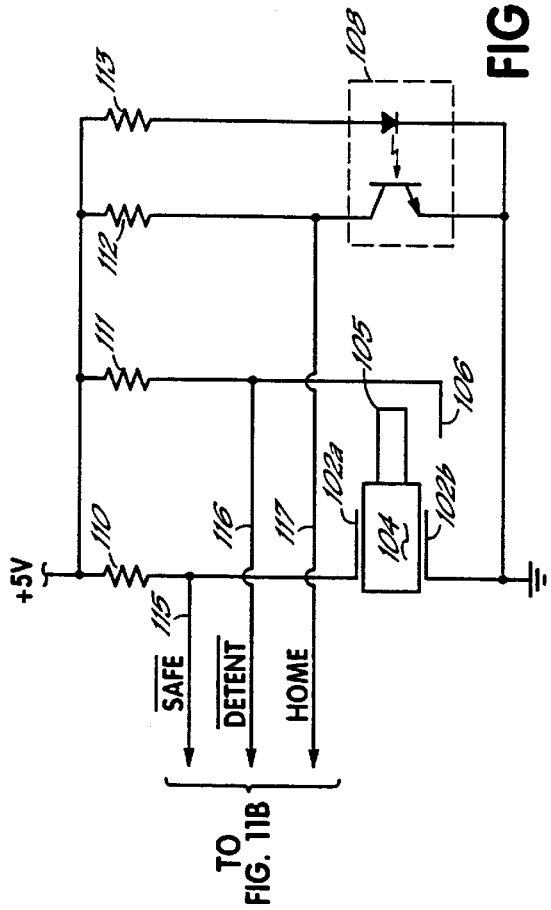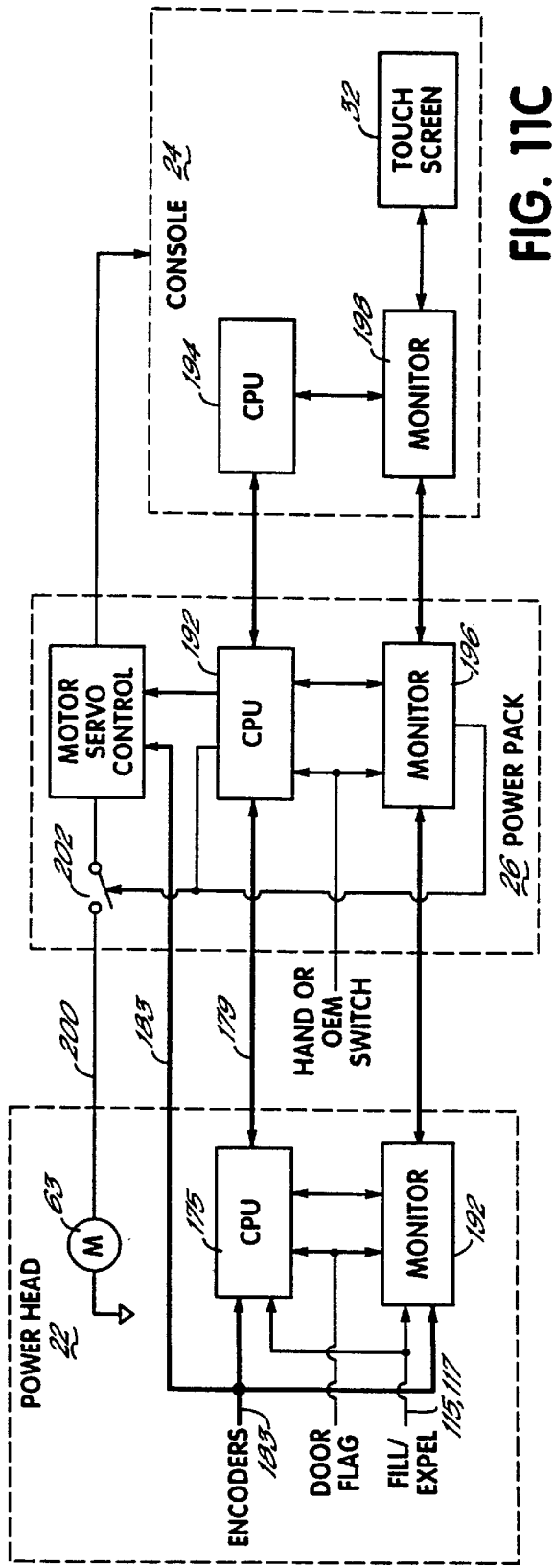

MEDICAL FLUID INJECTOR

This application is a divisional of U.S. application Ser. No. 08/753,288 filed Nov. 22, 1996, now U.S. Pat. No. 5,868,710, issued Feb. 9, 1999.

FIELD OF THE INVENTION

The present invention relates to injectors for injecting fluid into animals.

BACKGROUND OF THE INVENTION

In many medical environments, a medical fluid is injected into a patient during diagnosis or treatment. One example is the injection of contrast media into a patient to improve CT, Angiographic, Magnetic Resonance or Ultrasound imaging, using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling mounted arm.

The injection head is typically mounted on the arm in a pivotal manner, so that the head may be tilted upward (with the syringe tip above the remainder of the syringe) to facilitate filling the syringe with fluid, and downward (with the syringe tip below the remainder of the syringe) for injection. Tilting the head in this manner facilitates removal of air from the syringe during filling, and reduces the likelihood that air will be injected into the subject during the injection process. Nevertheless, the potential for accidentally injecting air into a patient remains a serious safety concern.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

Thus, at least part of the injection process is typically automatically controlled; however, the filling procedure, and typically some part of the injection procedure, are normally performed by an operator, using hand-operated movement controls on the injector head. Typically, the hand-operated movement controls include buttons for reverse and forward movement of the injector drive ram, to respectively fill and empty the syringe. In some cases, a combination of buttons is used to initiate movement of the ram or to control ram movement speed. The injector head also typically includes a gauge or display for indicating injection parameters to the operator, such as the syringe volume remaining, for the operator's use when controlling the injector head. Unfortunately, operators have found it cumbersome to use the hand-operated movement buttons and to read the injector head gauges and displays, for several reasons, not the least of which is the necessary tilting of the injector head between the upward, filling position to the downward, injection position, changing the positions of the hand-operated movement buttons relative to the operator, and at some tilt angles rendering the gauges or displays difficult to read.

In many applications, it is desirable to use an injector with multiple different syringe sizes. For example, it may be desirable to use a smaller syringe for pediatric use than for adult use. To facilitate the use of different syringe sizes, injectors have been constructed with removable face plates, where each of the various face plates is configured for a particular syringe size. Typically, the injector is able to adjust injection parameters by detecting which face plate is mounted to the injector, for example using a magnetic detector mounted to the front surface of the injector housing to detect the presence or absence of a magnet in the face plate. Unfortunately, the necessity of incorporating a magnetic detector into the outer housing of the injector head increases the complexity and expense of manufacturing the injector head.

SUMMARY OF THE INVENTION

In accordance with the invention, improvements are made on these various aspects of the operation of the typical injector.

In particular, an injector in accordance with the invention features an air bubble detection system positioned adjacent the tip of the syringe for detecting the presence of air in the tip of the syringe. This detection system, which is electrically connected directly to the control circuitry in the injector, permits the injector to detect air in the tip of the syringe, and if air is detected, to halt any prospective or ongoing injection. Since air is detected prior to exit from the syringe and before passage through the tubing leading to the patient, rather than at some intermediate point along the tubing, the injector is more likely to detect air early enough to prevent or halt the injection before the air reaches the patient.

In the specific disclosed embodiment, the air detector generates a light beam and directs this light beam into the tip of the syringe, where it is reflected from the inner wall of the syringe tip and returned into a detector. Other methods of air detection, such as ultrasonic air detection, may also be performed by a detector mounted at the syringe tip with similar advantage, and are encompassed within the scope of the invention.

Another aspect of this feature of the injector is the structure of the syringe tip, which includes an outwardly-projecting transparent section positioned for mechanical coupling to the source of light in the air detector, to facilitate light coupling into the syringe tip for reflection from the inner wall of the tip and return to the detector. This outwardly-projecting section forms a lens for focusing light impinging upon the syringe tip so that this light properly reflects through the interior of the syringe tip.

The injector in accordance with the present invention also features a hand-operated fill/expel control which facilitates operator control of the injector. The control includes a lever movable between home, forward, and reverse positions, where movement of the lever to the forward position causes the injector to move the plunger drive ram forward to expel fluid from the syringe, and movement of the lever to the reverse position causes the injector to move the plunger drive ram in reverse to draw fluid into the syringe.

In specific embodiments, the lever is mounted on a pivot, and biased to the home position by return springs positioned on opposite sides of the lever. Rotation of the lever away from the home position progressively bends the springs at increasing angles of lever rotation. A detector, specifically a rotary potentiometer, detects the angle of rotation of the lever, so that this angle can be used to control the speed of motion of the plunger drive ram. Using this structure and control, the relative position of the lever, and (if desired) the return torque applied by the springs to the lever, can be made roughly proportional to the flow rate of fluid into or out of the syringe, providing the operator with intuitive feedback on the operation of the injector. Alternatively, the injector may control the injection pressure produced by the injector in response to the angle of rotation of the lever, to provide the operator with feedback on the injection pressure being applied.

As a safety feature, in the disclosed specific embodiment, the return springs and lever are elements in an electrical circuit which produces a movement control signal. The central processing unit controlling the injector responds to this signal by displaying a fault message, or rendering the hand-operated movement control inoperative, if one of the springs breaks, so that in such a case the injector will not respond to unintentional displacement of the lever away from the home position which might result from breakage of a spring.

As an aid in filling the syringe, an additional detent spring is positioned relative to the lever in order to alter the return torque applied to the lever when the lever is rotated more than a given angle away from the home position. The result is a "detent" that can be identified by the operator, i.e., an angle at which the resistive torque increases dramatically. This detent angle can have any desired significance, but in the disclosed embodiment, this angle of rotation corresponds to a recommended maximum speed for filling the syringe, i.e. the largest speed at which fluid can be drawn into the syringe without dramatic increase in the generation of air bubbles. As with the other springs, the detent spring can be an electrical contact, used to produce a second control signal indicating that the lever has been rotated to the detent angle, so that the injector control circuitry can calibrate the speed at the moment the lever contacts the detent spring so that this lever position corresponds to the recommended maximum speed. Alternatively, the second control signal can be used to prevent the operator from attempting to fill the syringe at any faster rate.

To complement the intuitive feedback obtained from the above-described fill/expel lever, the injector in accordance with the present invention further features a tilt-compensating display. The injector head includes a tilt angle sensor for detecting the tilt angle of the head, and uses this tilt angle to choose one of two display orientations. As a result, the display is always oriented properly for reading by the operator, regardless of whether the injector is tilted upright for filling or down for injection.

In the specific disclosed embodiment, the display is a light emitting diode display having elements arranged so that the display can provide the same information in either an upright or inverted orientation. However, other embodiments are contemplated, such as the use of a liquid crystal display, or a pixilated display permitting full variation in display attributes and orientations.

As further aspects of this feature, the tilt-sensing circuitry in the injector is also used to ensure proper operation of the injector. For example, the range of fill and expel speeds available from the hand-operated movement control is broader when the injector head is tilted upward than when the head is tilted downward. Furthermore, the injector prevents automatic injection unless the injector head is tilted downward, and/or the injector warns the operator of possible air injection when the head is not tilted at a sufficient downward angle.

The injection head in accordance with the invention has a compact, modular design facilitating manufacture and service. In particular, to the extent possible all control circuitry has been incorporated onto a single printed circuit board. Notably, one feature of the inventive injector is the use of magnetic conductors to channel magnetic field energy from magnets positioned in the injector face plate, through the injector housing and into the vicinity of magnetic detectors (e.g., Hall effect switches) mounted on the main circuit board. By using magnetic conductors to carry magnetic fields through the injector housing, circuit-board-mountable magnetic detectors can be used, substantially reducing the overall cost as compared to purchasing individually packaged detectors for mounting in the injector housing.

In addition to the safety features identified above, the injector in accordance with the present invention includes a hardware safety feature for detecting processor or software failures and preventing erroneous injections. Specifically, the injector head includes a central processing unit for controlling all functions of the injector head, and a monitor microcontroller for monitoring the operation of the central processing unit. The central processing unit delivers information on its state of operation to the monitor microcontroller. The monitor microcontroller also monitors the hand-operated controls on the injector head and the movements of the injector drive ram to confirm that these controls and movements are consistent with the processor state reported by the central processing unit. If the two do not agree, the monitor microcontroller can halt operation of the injector head.

In the specific disclosed embodiment, there are central processing units in each of the injector head, console and power pack, which communicate with each other to operate the injector in its various modes, and each central processing unit is associated with a monitor microcontroller, and the monitor microcontrollers similarly intercommunicate to ensure that the central processing units are functioning correctly individually and collectively.

The above and other features, aspects, objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 6 is a perspective, partial sectional view of the hand-operated control assembly;

FIG. 7C is an electrical schematic diagram of the electrical circuit formed by the hand-operated control lever, return and detent springs;

FIG. 11C is an electrical block diagram of the central processing units and microcontrollers in the power head, power pack and console and their interconnection;

DETAILED DESCRIPTION OF SPECIFIC EMBODIMENTS

Figure 1:
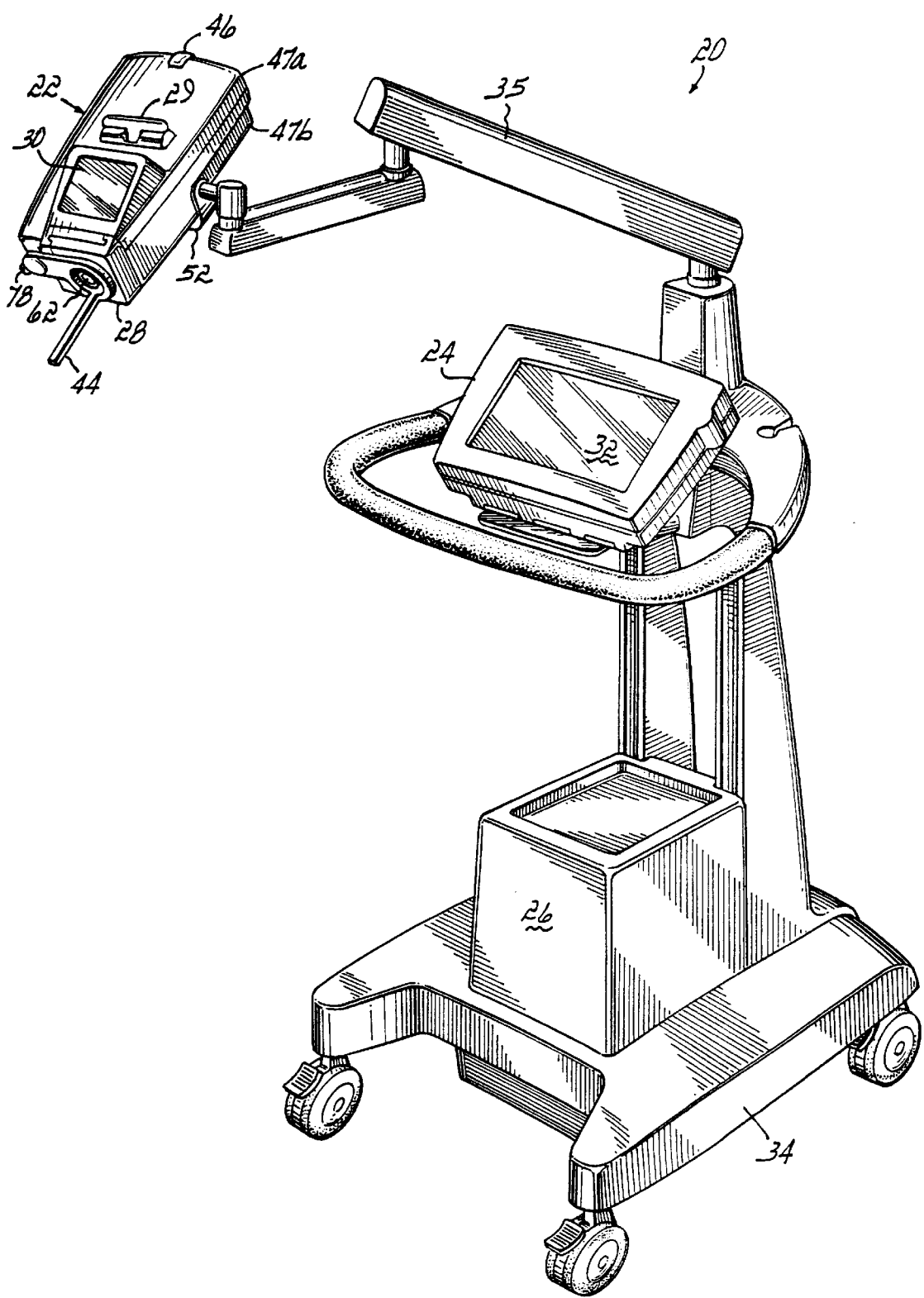
FIG. 1 is a perspective view of an injector in accordance with principles of the present invention, including a power head, console, and power pack (under a cover), with the syringe, pressure jacket, heater blanket and air detection module removed.

Referring to FIG. 1, an injector 20 in accordance with the present invention includes various functional components, such as a power head 22, a console 24 and power pack 26 (mounted inside of a cover). A syringe 36 (FIG. 2) is mounted to the injector 20 in the face plate 28 of the power head 22, and the various injector controls are used to fill the syringe with, e.g., contrast media for a CT, Angiographic or other procedure, which media is then injected into a subject under investigation under operator or pre-programmed control.

The injector power head 22 includes a hand-operated movement control lever 29 for use in controlling the movement of the internal drive motor, and a display 30 for indicating to the operator the current status and operating parameters of the injector. The console 24 includes a touch screen display 32 which may be used by the operator to remotely control operation of the injector 20, and may also be used to specify and store programs for automatic injection by the injector 20, which can later be automatically executed by the injector upon initiation by the operator.

Power head 22 and console 24 connect through cabling (not shown) to the power pack 26. Power pack 26 includes a power supply for the injector, interface circuitry for communicating between the console 24 and power head 22, and further circuitry permitting connection of the injector 20 to remote units such as remote consoles, remote hand or foot control switches, or other original equipment manufacturer (OEM) remote control connections allowing, for example, the operation of injector 20 to be synchronized with the x-ray exposure of an imaging system.

Power head 22, console 24 and power pack 26 are mounted to a carriage 34 which includes a support arm 35 for supporting power head 22 for easy positioning of power head 22 in the vicinity of the examination subject. Other installations are also contemplated however; for example, console 24 and power pack 26 may be placed on a table or mounted on an electronics rack in an examination room while power head 22 is supported by a ceiling, floor or wall mounted support arm.

Figure 2:
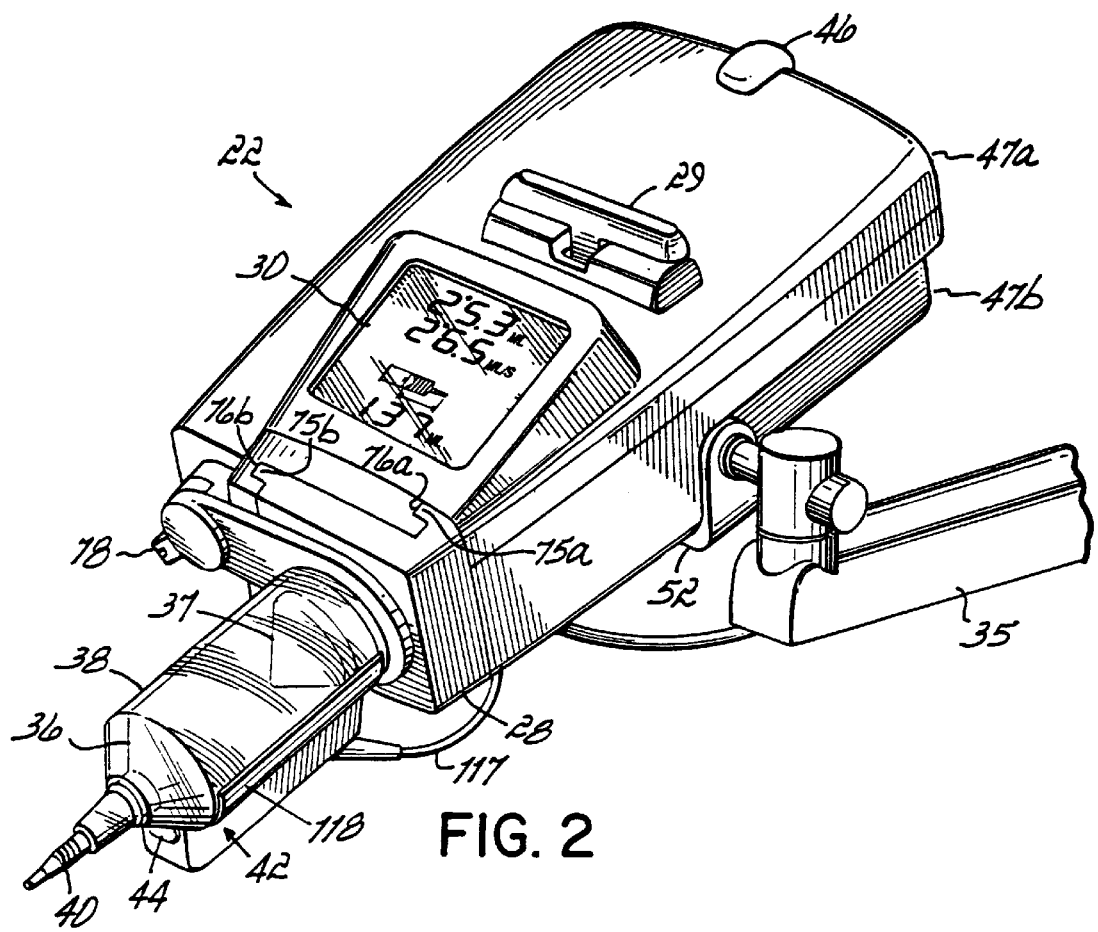
FIG. 2 is a perspective view of the power head of the injector of FIG. 1 with a pressure jacket, syringe and heater blanket mounted thereto, showing the power head display, hand-operated control, and support arm mounting in greater detail.

Referring now to FIG. 2, in operation, a syringe 36 and pressure jacket 38 are mounted to power head 22, so that the motor internal to power head 22 may be energized to move a plunger 37 within the barrel of syringe 36 toward and away from a discharge tip 40 of the syringe, to thereby expel fluid from the syringe 36 or fill the syringe with fluid. Pressure jacket 38 provides support to the outer walls of syringe 36 to protect the walls of syringe 36 from failure at high injection pressures.

Syringe 36 and pressure jacket 38 are made of a clear plastic material through which the operator can view the current location of plunger 37 and any fluid or air in the syringe between plunger 37 and discharge tip 40. Accordingly, as described above, an operator may tilt power head 22 upward, fill syringe 36 from a source of fluid while visually monitoring the filling process, then connect the injector to tubing leading to the patient, expel air from the tubing and syringe while visually monitoring the level of fluid in the syringe, and then once air has been expelled, tilt the injector downward and proceed to inject fluid into a subject.

To facilitate this filling process, and other operations that may be performed during injection of a subject, power head 22 includes the hand-operated movement control, which is in the form of the rotatable lever 29. Specifically, lever 29 is rotatable on an axis of rotation inside of power head 22. When the hand-operated control lever 29 is left in its home position, illustrated in FIG. 2, no plunger motion is generated by power head 22. However, when hand-operated control lever 29 is rotated toward syringe 36, forward plunger motion is generated by power head 22, expelling fluid or air from syringe 36. Alternatively, when hand-operated control lever 29 is rotated away from syringe 36, reverse plunger motion is generated by power head 22, filling syringe 36 with fluid or air. Further details on the construction and operation of hand-operated control lever 29 will be elaborated below in connection with FIGS. 6–7C.

To ensure that fluid injected into a subject is maintained at approximately body temperature, a heater blanket 42 is installed abutting the exterior wall of pressure jacket 38. Heater blanket 42 includes an electrical heater which generates heat for regulating the temperature of fluid within syringe 36. Heater blanket 42 (which is separately illustrated in FIG. 8) is mounted to a post 44 extending from face plate 28, holding heater blanket 42 in thermal contact with pressure jacket 38.

At the rear end of power head 22 is an indicator lamp 46 (covered by a light-diffusing cover) which indicates the status of the power head, as discussed in further detail below.

Figure 3:
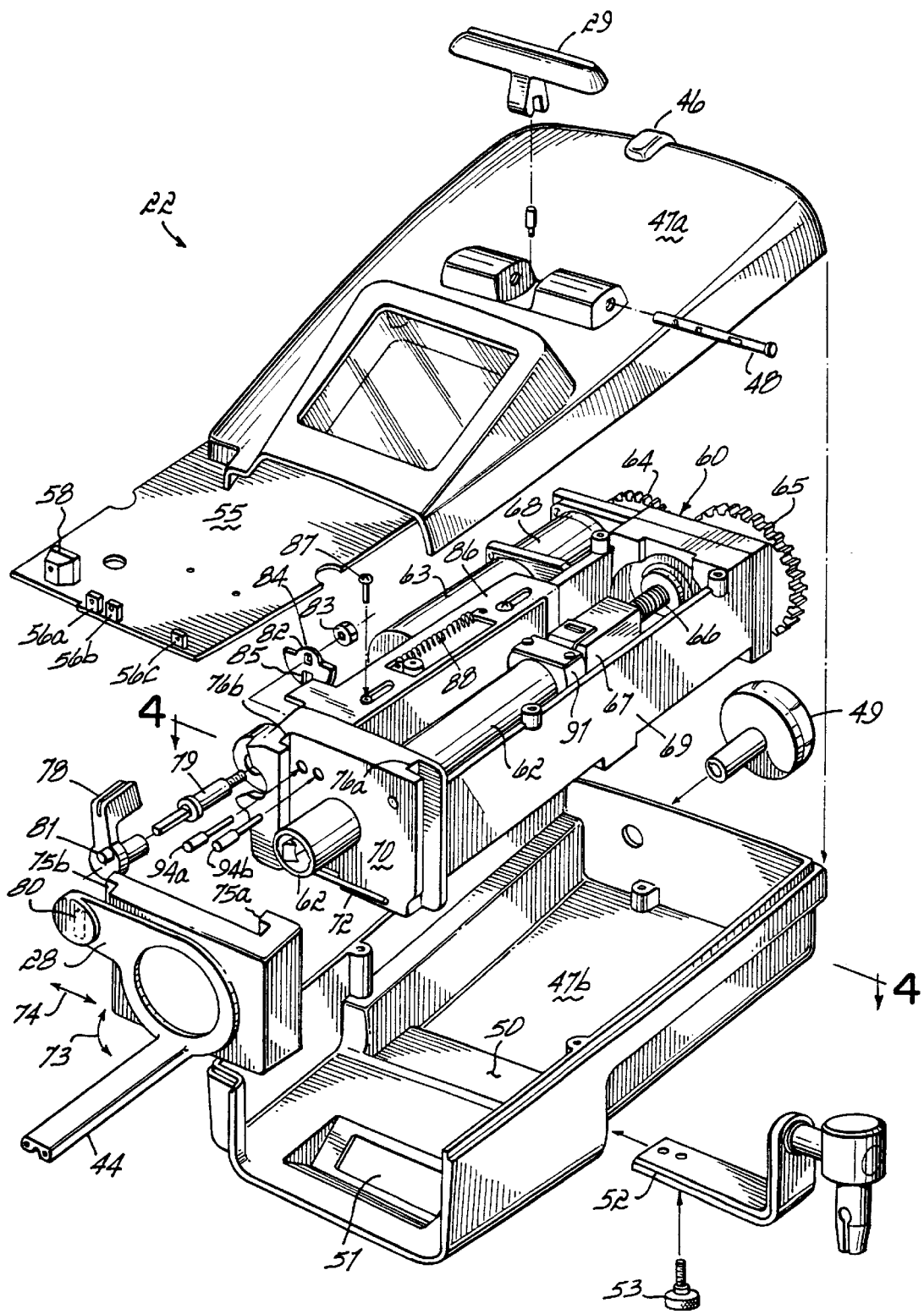
FIG. 3 is a disassembled view of the internal structure of the power head of FIG. 2 illustrating details of the face plate, circuit board, plunger ram drive and housing.

Now referring to FIG. 3, the internal structure of the power head 22 can be described.

Power head 22 is constructed from two external half-housings 47a and 47b. Half-housings 47a and 47b mate to form the complete housing for power head 22. The upper half-housing 47a includes an aperture through which the display 30 can be viewed, the indicator lamp 46, and bearing surfaces for supporting a shaft 48 to which hand-operated control lever 29 is attached. Details of the hand-operated control lever structure mounted internally to upper half-housing 47a are discussed in further detail below.

Lower half-housing 47b includes an aperture through which a knob 49 is mounted and coupled to the internal drive train. Knob 49 can be rotated by hand to move the drive train of the plunger drive ram, to allow precise control of ram movements, and also to permit movement if an electrical failure disables the power head 22. A second aperture 51 in lower half-housing 47b is used to connect the power head circuit board 55 (see below) to electrical lines leading from the heater blanket 42 (see FIGS. 2, 8) and air detector attachment (see FIGS. 9, 10).

Lower half-housing 47b further includes a mounting track (opposite to indentation 50 inside of half-housing 47b) for receiving a mount 52 for supporting half-housing 47b on an articulated arm such as arm 35 shown in FIGS. 1 and 2. Mount 52 may be inserted into the mounting track of lower half-housing 47b from either side of power head 22, facilitating mounting of power head 22 on either side of an examination table. A knob 53 holds mount 52 in place in the mounting track in lower half-housing 47b.

Internal features of power head 22 include a circuit board 55 which supports substantially all of the electrical circuitry for controlling the operations of power head 22. Notable components found on circuit board 55 include magnetic detectors 56a, 56b and 56c and flag sensor 58. The main circuit board also includes the indicator lamp 46 (not shown). The functions of detectors 56a, 56b and 56c and flag sensor 58 will be elaborated more fully below.

Mounted below circuit board 55 inside of power head 22, is the drive train 60 for the plunger drive ram 62. Drive train 60 includes a rotary electric motor 63, controlled by circuit board 55, which (via a gear box 68) rotates a drive pinion 64. Pinion 64 meshes with a main gear 65, which rotates a ball screw 66. Plunger drive ram 62 is mounted to a ball screw nut 67 which converts rotation of ball screw 66 into linear translation of plunger drive ram 62 into or out of power head 22, thus moving the plunger 37 (FIG. 2) of a syringe 36 mounted to power head 22. Knob 49 is coupled to the axis of drive pinion 64, thus permitting hand rotation of the drive train 60 and motion of the plunger drive ram.

These elements of the drive train 60 are mounted to a drive housing 69. When the upper and lower half-housings 47a and 47b are assembled around the drive housing 69, the front surface 70 of drive housing 69 is exposed. The face plate 28 of the injector is attached to front surface 70, to allow a syringe to be mounted to the front surface 70 of the drive housing 69 so that plunger drive ram 62 may engage and move the syringe plunger 37.

The face plate 28 is attached to front surface 70 by a hinged connection, using a hinge pin 72. When face plate 28 has been attached to front surface 70 with hinge pin 72, face plate 28 may rotate in direction 73 on hinge pin 72, and may also translate in direction 74 over a limited distance along hinge pin. This combination of rotational and translational movement allows face plate 28 to be is engaged and disengaged from front surface 70, permitting loading and removal of syringes from face plate 28, and simultaneous coupling and uncoupling of the syringe plunger from plunger drive ram 62.

When face plate 28 is fully engaged to front surface 70, tabs 75a and 75b on face plate 28 mate to slots 76a and 76b, respectively, on front surface 70. This mating relation is shown in greatest detail in FIG. 4. To disengage face plate 28 from front surface 70, face plate 28 is translated along direction 74 to disconnect tabs 75a and 75b from slots 76a and 76b, permitting face plate 28 to rotate on hinge pin 72 in direction 73 (FIG. 3), thus permitting access to a syringe mounted to face plate 28.

To facilitate translation of face plate 28 along direction 74, a cam lever 78 is mounted to drive housing 69 between face plate 28 and drive housing 69. Cam lever 78 is affixed to and rotates a cam lever shaft 79, which is mounted in drive housing 69. Cam lever 78 includes a button 81 which projects toward face plate 28. Button 81 mates with a channel 80 formed in the inner surface of face plate 28 (see FIG. 4), so that rotation of cam lever 78 causes button 81 to translate face plate 28 along direction 74, engaging or disengaging tabs 75a and 75b from slots 76a and 76b.

A flag washer 82 is mounted to cam lever shaft 79 and held in place with a nut 83. The apertures in flag washer 82 and cam lever 78 which connect to cam lever shaft 79 are keyed, so that cam lever 78 and flag washer 82 are oriented in a consistent manner relative to each other. Because flag washer 82 and cam lever 78 are both keyed to shaft 79, rotation of cam lever 78 will cause shaft 79 and flag washer 82 to rotate. Flag surface 84 extends from flag washer 82; movement of this flag surface due to rotation of cam lever 78 is detected as noted below and used to determine whether face plate 28 is engaged to the power head 22.

Figure 4:
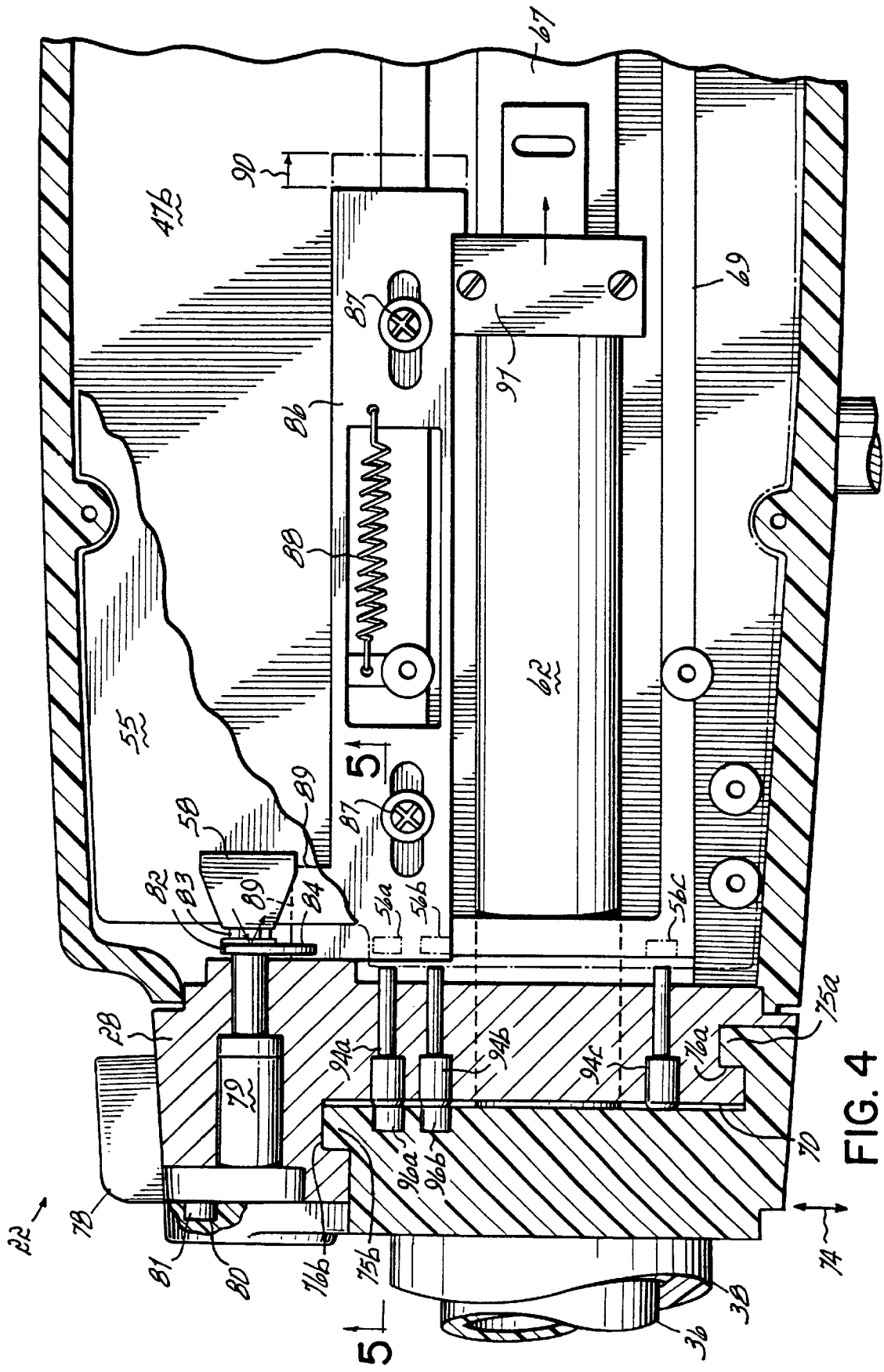
FIG. 4 is a partial sectional view of the internal structure of an assembled power head, taken along lines 4—4 in FIG. 3.

Referring now to FIGS. 3 and 4, when power head 22 is assembled as shown in FIG. 4, flag washer 82 is positioned opposite to flag sensor 58 on circuit board 55. Flag sensor 58 produces a light beam which, when flag surface 84 is opposite to sensor 58, will be reflected and detected by sensor 58. Cam lever 78 and flag washer 82 are keyed into shaft 79 so that flag surface 84 is rotated opposite to detector 58 only when cam lever 78 is positioned as shown in FIG. 4, in which position cam lever 78 will have translated cam face plate 28 into engagement with the front face 70 of drive housing 69, permitting injection. Thus, when flag surface 84 is opposite to flag sensor 58, this indicates that the face plate is in the closed position, ready for filling or injection.

Power head 22 includes a safety lock-out which prevents rotation of cam lever 78 to a disengaged position when plunger drive ram 62 is other than fully retracted. Specifically, referring to FIG. 4, a spring loaded lockout plate 86 is mounted to drive housing 69 in a manner to permit translational movement in direction 90. Screws 87 hold lockout plate 86 in position on drive housing 69 to allow this translational movement. Spring 88 is coupled between lockout plate 86 and drive housing 69 to provide force tending to slide lockout plate 86 toward front surface 70 of drive housing 69, i.e., into the position shown in FIG. 4.

When lockout plate 86 is in this forward most position, the front corner 89 of lockout plate 86 is positioned adjacent to flag washer 82, as seen in FIG. 4. As a result, interference between a notch 85 (see FIG. 3) in flag washer 82 and front corner 89 of lockout plate 86 prevents rotation of flag washer 82 (and cam lever 78) from the engaged position shown in FIG. 4 to a position where face plate 28 will disengage from front surface 70 of drive housing 69, and can be rotated away from front surface 70 to replace a syringe. However, when lockout plate slides backward in direction 90 (against the force of spring 88), this interference between front corner 89 and notch 85 in flag washer 82 is eliminated, allowing cam lever 78 to rotate to a disengaged position.

A fitting 91 on plunger drive ram 62 is positioned to engage to lockout plate 86, so that when plunger drive ram 61 is withdrawn from the face plate 28 to a fully rearward position, fitting 91 will engage lockout plate 86 and move it to its backward position. However, when plunger drive ram 62 is moved forward from this position, the force of spring 88 moves lockout plate into its forward position. Thus, as a result of the interaction of plunger drive ram 62, lockout plate 86 and flag washer 82, face plate 28 cannot be translated in direction 74 or disengaged from front surface 70 of drive housing 69 unless the plunger drive ram 62 is at its fully rearward position. This interlock prevents the operator from attempting to disengage face plate 28 from front surface 70 while plunger drive ram 62 is projecting inside of a syringe mounted to face plate 28.

Figure 5:
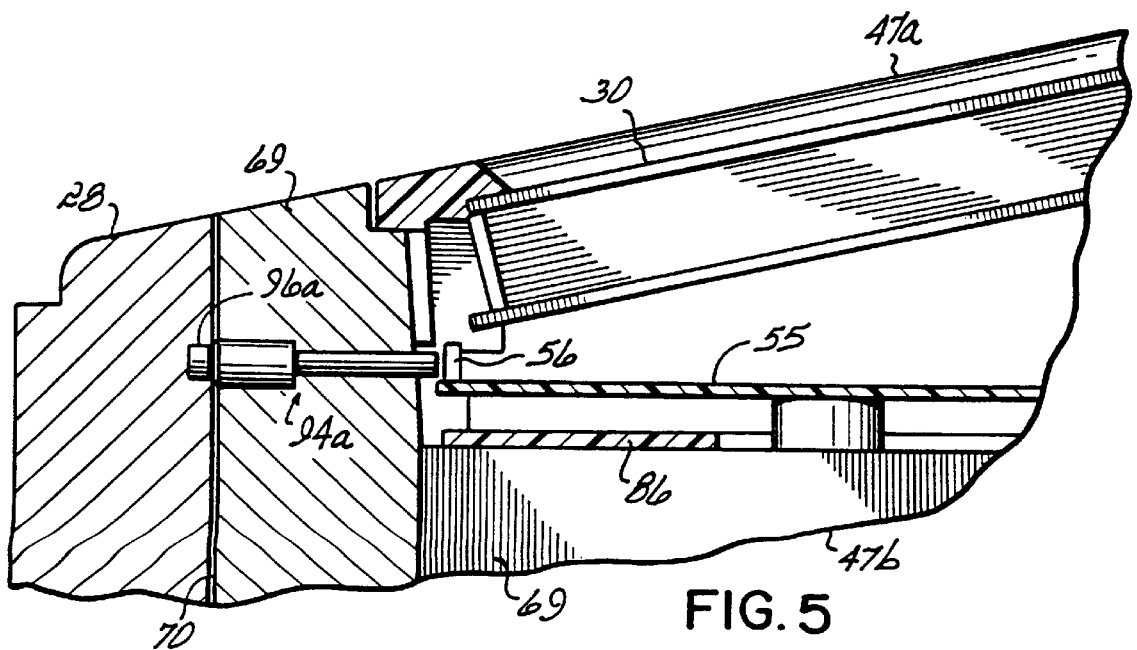
FIG. 5 is a partial sectional view taken along lines 5—5 of FIG. 4, showing the relative positions of the circuit board, housing, display and magnetic conductors within the housing.

Referring now to FIGS. 4 and 5, there is illustrated three magnetic conductors 94a, 94b and 94c. These conductors are manufactured of a high permeability, low retentivity material such as steel or iron, and are inserted through apertures in the front surface 70 of drive housing 69.

Each face plate 20 may be provided with permanent magnets inserted at positions which are in registration with the positions of the three magnetic conductors 94a, 94b and 94c. There may be three, two, one or no permanent magnets, and the magnets may be oriented with their North or South poles facing magnetic conductors 94a, 94b and 94c.

The face plate 28 shown in FIG. 4 includes two permanent magnets 96a and 96b positioned in registration with magnetic conductors 94a and 94b. The face plate shown in FIG. 4 does not, however, have a magnet positioned opposite to magnetic conductor 94c.

Multiple different face plates 28 may be used with the power head 22 illustrated in FIGS. 3 and 4. Different face plates 28 may be used to adapt the power head 22 to use different types of syringe 36; for example, one face plate may be sized for use with low capacity pediatric syringes, whereas another is sized for use with adult-capacity syringes. Pre-filled syringes may have different sizes or dimensions than syringes which are purchased empty. Different face plates 28 are needed to accommodate these different syringe sizes.

It is necessary for the control circuitry on circuit board 55 to be able to detect which face plate is installed on power head 22. Firstly, the control circuitry must determine whether an air detection module is attached to the face plate. Also, different syringe 36 types may have differing lengths, in which case power head 22 must be able to compensate for the length variations when determining the end-of-travel position of the plunger drive ram and when computing the volume of fluid in the syringe 36. Similarly, syringes of different diameters will produce different flow rates for the same rate of travel of the plunger drive ram 62; the control circuitry must compensate for this when converting a requested flow rate into movement of the plunger drive ram 62.

For identification purposes, each different face plate 28 has a unique combination of permanent magnets installed therein, in registration with the magnetic conductors 94a, 94b and 94c in the front surface 70 of the drive housing 69. Specifically, the face plate illustrated in FIG. 4 has two permanent magnets, opposite conductors 94a and 94b.

Another face plate might have only one permanent magnet, positioned opposite conductor 94b. A third face plate might have three permanent magnets positioned opposite all three conductors 94a, 94b and 94c. There are twenty-seven ($3^3$) possible combinations of magnets, or the lack thereof, at alternative polarities, that can be created, and thus twenty-seven different face plates can be uniquely identified in this manner.

To detect the number and positioning of permanent magnets in the face plate, the control circuit of the power head 22 includes magnetic detectors 56a, 56b and 56c, which may for example be Hall effect sensors (or, alternatively, reed switches). These three magnetic detectors 56a, 56b and 56c are positioned near an edge of circuit board 55 in registration with the inner ends of the three magnetic conductors 94, as can be seen by comparing FIGS. 4 and 5. Typically, the drive housing 69 is manufactured of a non-magnetic material such as Aluminum. Accordingly, magnetic fields produced by permanent magnets 96a and 96b are channeled through the magnetically permeable conductors 94a, 94b and 94c, and thus brought into the vicinity of detectors 56a, 56b and 56c, so that the presence or absence of permanent magnets in face plate 28 can be detected remotely from the face plate 28 by detectors on circuit board 55.

The magnetic conductors, by channeling magnetic fields from permanent magnets in the face plate 28 to remotely located detectors on circuit board 55, provide a substantial reduction in cost of the electronic portion of the power head 22. Although free-standing magnetic detectors are available, and could be mounted to the front surface 70 of drive housing 69, free-standing magnetic detectors are typically substantially more expensive to purchase than printed circuit board mountable detectors. Furthermore, the use of free-standing magnetic detectors would entail manufacturing multiple separate circuit boards and/or harnesses and installing them in the power head housing with appropriate cabling connections to the main circuit board, which would make the manufacture of power head 22 more complex, expensive and time-consuming, as compared the present embodiment where the detectors are included on the main circuit board. Accordingly, the use of magnetic conductors 94a, 94b and 94c substantially reduces the cost of manufacturing power head 22.

Referring to FIG. 6, the details of the hand-operated movement control can be explained. As noted above, hand-operated control lever 29 is rotated in a forward direction or reverse direction to indicate the operator's desire to move the plunger drive ram forward or in reverse. To determine the direction and degree of rotation of lever 29, a rotary potentiometer 98 is coupled to shaft 48 of lever 29, so that rotation of lever 29 rotates a wiper inside of potentiometer 98, creating a changing resistance that can be detected by the power head control circuitry.

As noted above, when control lever 29 is rotated forward in direction 99, the control circuitry, detecting this rotation from electrical signals produced by potentiometer 98, causes the plunger drive ram 62 to move forward, i.e., outward from the power head housing, at a velocity proportional to the angle of deflection of control lever 29 away from the home position shown in FIG. 6. Alternatively, when control lever is rotated in a reverse direction 100, the control circuitry detects this rotation from electrical signals produced by potentiometer 98, and causes the plunger drive ram 62 to move backward, i.e., into the power head housing, at a velocity proportional to the angle of deflection of control lever 29 away from the home position shown in FIG. 6.

FIG. 6 illustrates the two return springs 102a and 102b which engage shaft 48 and produce torque tending to return shaft 48 to the home position shown in FIG. 6. Also shown is the combined flag/contact 104 which surrounds shaft 48 and contacts return springs 102a and 102b. Return springs 102a and 102b make contact with flag/contact 104 and thereby form an electrical connection to each other, and also apply spring torque tending to return shaft 48 to the home position. Also seen are detent spring 106, the function of which will be elaborated below, and flag detector 108, which is an optical detector which generates a light pulse for transmission across a gap, detects receipt of the light pulse on the opposite side of this gap, and generates a digital signal indicative of whether the gap is obstructed in such a way as to prevent light transmission.

Figure 7A:
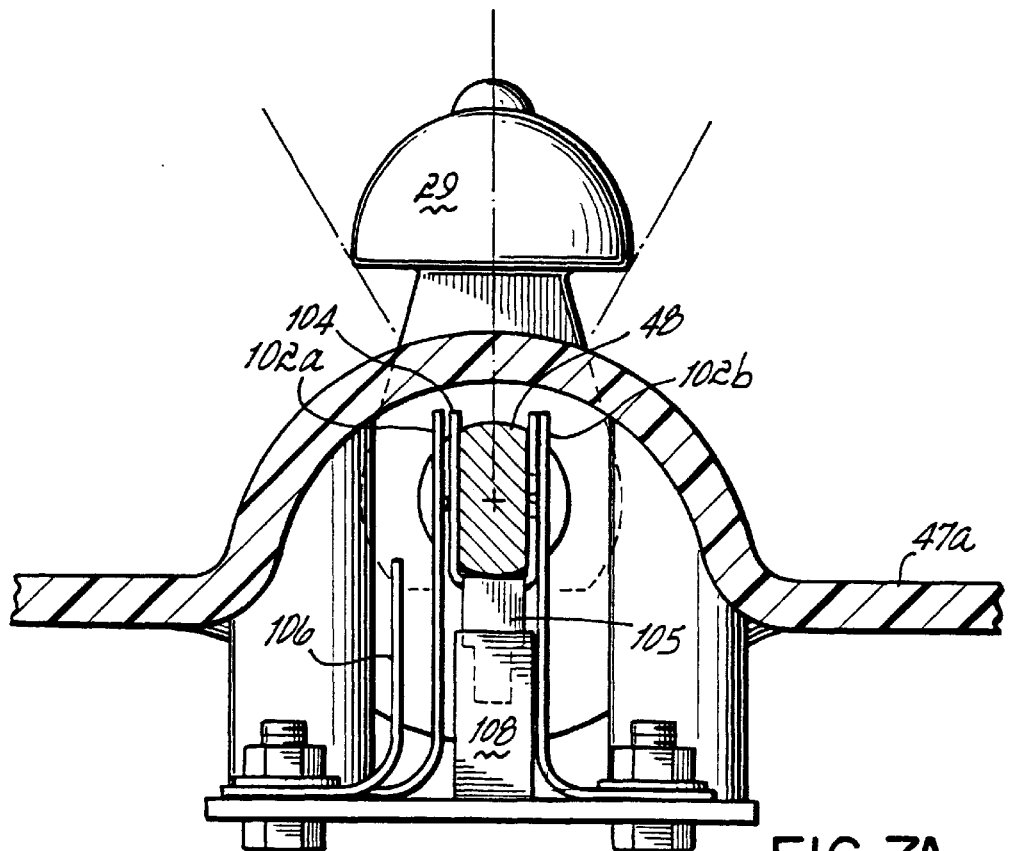
FIG. 7A is a cross-sectional view of the hand-operated control assembly of FIG. 6 taken along lines 7A—7A of FIG. 6, showing the return and detent springs.
Figure 7B:
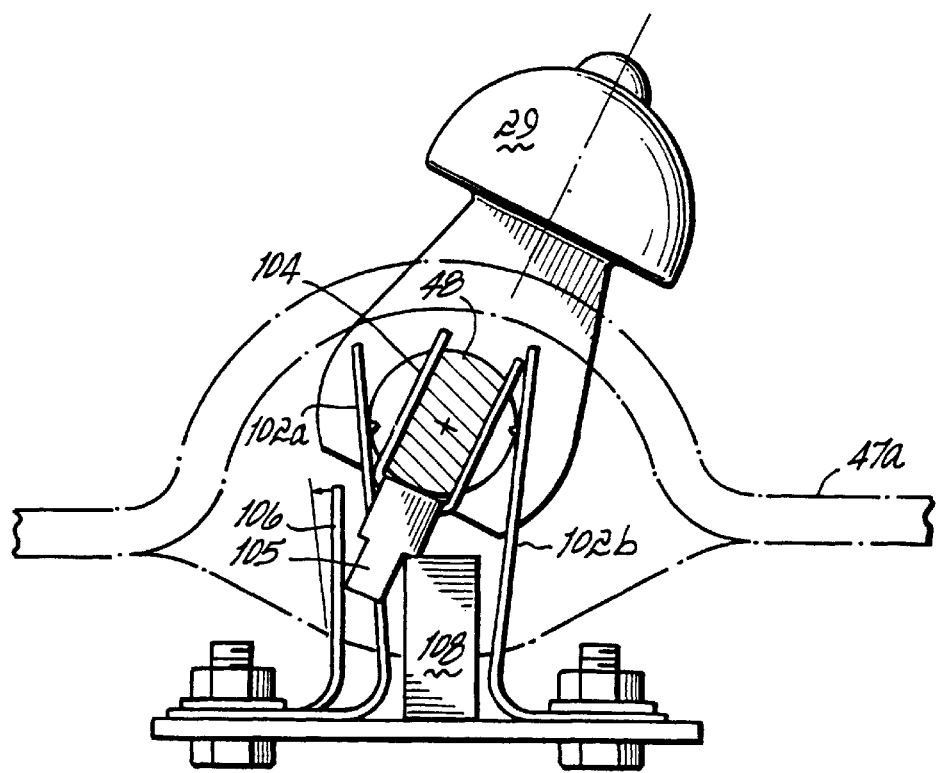
FIG. 7B is a cross-sectional view of the hand-operated control assembly showing the hand-operated control lever displaced from the home position and into contact with the detent spring.

Referring now to FIGS. 6, 7A and 7B, it can be seen that when lever 29 is in its home position (see FIGS. 6 and 7A), flag/contact 104 is positioned equidistant between return springs 102a and 102b, which apply opposing torques to lever 29, tending to hold lever 29 in this home position. In this position, flag 105 of combined flag/contact 104 is positioned inside of flag sensor 108, causing sensor 108 to produce a digital signal indicating that the lever is in its home position. In this case, the control circuit of power head 22 can determine that no plunger motion is being requested through the hand-operated movement control.

However, when lever 29 is rotated from its home position, such as in FIG. 7B, flag 105 moves outside of the gap formed by flag sensor 108, causing flag sensor 108 to produce a digital signal indicating that lever 29 is away from the home position. In this case, the control circuit may read the electrical signal produced by potentiometer 98 to determine the position of the lever and produce the appropriate motion of the plunger drive ram.

As noted above, the velocity of motion of the plunger drive is proportional to the extent of rotation of lever 29 away from its home position. At the same time, the mechanical structure of return springs 102a and 102b ensures that a return torque is applied to lever 29 as lever 29 is rotated to increasing angles away from the home position. Depending on the stiffness of springs 102a and 102b, and the range of motion of lever 29, this return torque may be approximately equal at all deflection angles, or may increase or decrease over increasing deflection angles. An increasing return torque with deflection angle, may be useful in providing the operator with additional feedback on the plunger velocity.

As can be seen in FIG. 7B, as lever 29 is rotated to increasing angles in the reverse direction, ultimately flag 105 contacts detent spring 106 and begins deflecting detent spring 106 as well as return springs 102a and 102b. This leads to an increase in applied torque that is detectable to the operator, as a "detent" in the rotation of the hand-operated movement control.

When filling a syringe, there is an ideal maximum speed at which fluid can be drawn into the syringe without forming air bubbles in the fluid due to non-laminar flows. To speed the filling of syringes, the operator should have feedback as to when this ideal speed has been reached, so that syringes can be filled at this optimal speed. The purpose of the detent spring 106, is to provide the operator with mechanical feedback of the angle of deflection of lever 29 which corresponds approximately to the ideal fill speed. More specifically, the control circuit of power head 22 establishes that the plunger drive will move at near to the ideal fill speed when lever 29 has been rotated such that flag 105 is in contact with detent spring 106. Accordingly, an operator wishing to fill a syringe at a near ideal speed, can rotate lever 29 until the increasing torque of the detent is noted, and then hold lever 29 at the detent location to fill the syringe.

The return springs 102, flag/contact 104 and return spring 106 are not only mechanically active to provide mechanical feedback to the operator, but are also electrical elements in the control circuit of power head 22. Specifically, referring to FIG. 7C, each of these elements is an electrical circuit element in a circuit for producing digital control signals used by the control of power head 22.

As seen in FIG. 7C, return springs 102a and 102b, and the flag/contact therebetween, are connected with a resistor 110 in a series connection between a digital +5 volt power supply and ground. A signal line 115 extending from between resistor 110 and spring 102a carries a logic voltage signal indicating whether a current-carrying electrical contact is completed between springs 102a and 102b and flag/contact 104. Under normal conditions, there should be an electrical path through this path to ground, holding the voltage on line 115 at a low level, indicating proper operation. However, if one of springs 102a or 102b fails, and no longer engages flag/contact 104, this electrical contact will be broken, and the voltage on line 115 will be elevated to a high level, indicating failure of a return spring. Although both return springs must fail before lever 29 may unintentionally deflect away from the home position, failure of just one spring can be detected by monitoring the voltage on line 115. Upon initial detection of such a failure, a warning may be given to the operator, or alternatively, the hand-operated movement control may disabled.

In a similar fashion, the detent spring 106 forms an electrical contact in a series connection with a resistor 111, and a detent signal line 116 extends from between resistor 111 and the detent spring. If control lever 29 is not rotated into the detent spring, line 116 will be pulled to a high level, indicating that the control lever 29 is not at the detent. However, if control lever 29 is rotated such that flag 105 contacts detent spring 106, line 116 will be pulled to a low level, indicating that control lever 29 has been rotated to the detent. The signal on line 116 may be used in several ways. For example, the signal may be used to calibrate the hand-operated control so that the angle of lever rotation corresponding to the detent is equal to the ideal fill speed. Alternatively, the signal may be used to prevent reverse movement of the ram at a speed faster than the ideal fill speed. Finally, the signal may be used to establish a "dead zone" of motion, in which the ram will move at the ideal fill speed, while permitting the lever to be rotated beyond the "dead zone" to produce faster reverse speeds.

FIG. 7C also illustrates the circuit details of th e flag detector 108; a light emitting diode is energized with a bias current via resistor 113; when light passes through the gap in detector 108 and strikes the base of a phototransistor in detector 108, the phototransistor draws current through resistor 112 to drive a home signal on line 117 to a low value, indicating that control lever 29 is not in its home position. Otherwise, if light is unable to pass to the base of the phototransistor in detector 108, current is not drawn through resistor 112 and the home signal on line 117 is pulled to a high value, indicating that control lever 29 is in its home position. The control circuitry for power head 22 can thus use the home signal on line 117 to determine whether to discontinue motion of the plunger drive ram.

Figure 8:
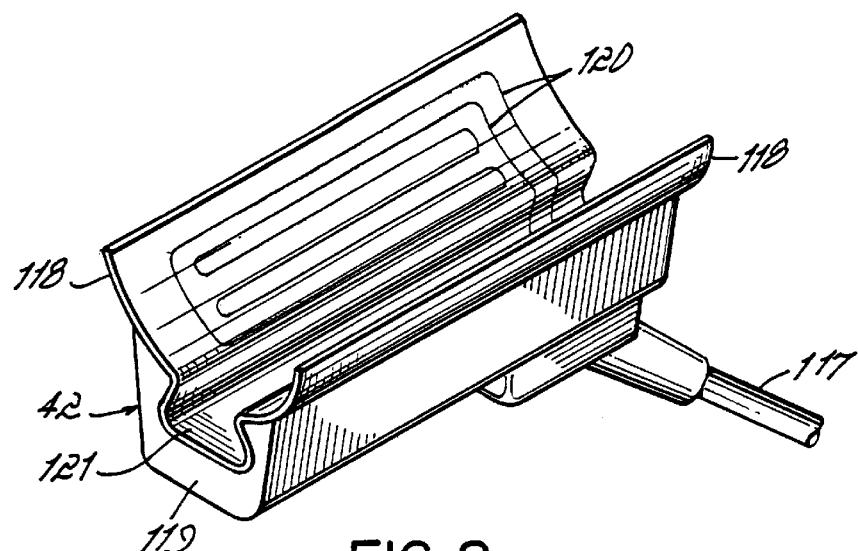
FIG. 8 is a perspective drawing of the heater blanket used to warm fluid in the syringe mounted to the injector.

Referring now to FIG. 8, the heater blanket 42 used with the power head 22 in accordance with the present invention, includes an annular plastic section 118 and a molded plastic base. Plastic section 118 includes a filament 120 of electrically resistive wire, which generates heat when an electrical current is driven through it via a suitable electrical power source. Filament 120 extends throughout the region of annular section 118 which is in contact with pressure jacket 38 when heater blanket 42 is mounted to post 44 as shown in FIG. 2, and terminates at either end in electrical leads encased in an insulating cable 117 which can be plugged into the power head 22 control circuitry through aperture 51 (FIG. 3) as is illustrated in FIG. 2. When current from the power head is forced through the leads in cable 117 and through the filament 120, filament 120 generates an even heat which warms fluid inside of the syringe in pressure jacket 38.

Annular section 118 might be opaque, or may be clear or translucent. If annular section 118 is clear, filament 120 could be seen through (as in an automobile defroster or a window screen) so that the operator is better able to visualize fluid inside of the syringe through the annular section, pressure jacket 38 and syringe wall. This may be advantageous in applications where the operator's primary line of sight to the interior of the syringe might otherwise be obscured by the heater blanket.

Base 119 of heater blanket is formed of a soft plastic, overmolded on a resilient skeleton. The resilient skeleton is shaped with a bowl 121 sized for a slight interference fit with post 44. As a result, heater blanket 42 may be snap fit over post 44 for convenient installation and removal (e.g., for cleaning).

Figure 9:
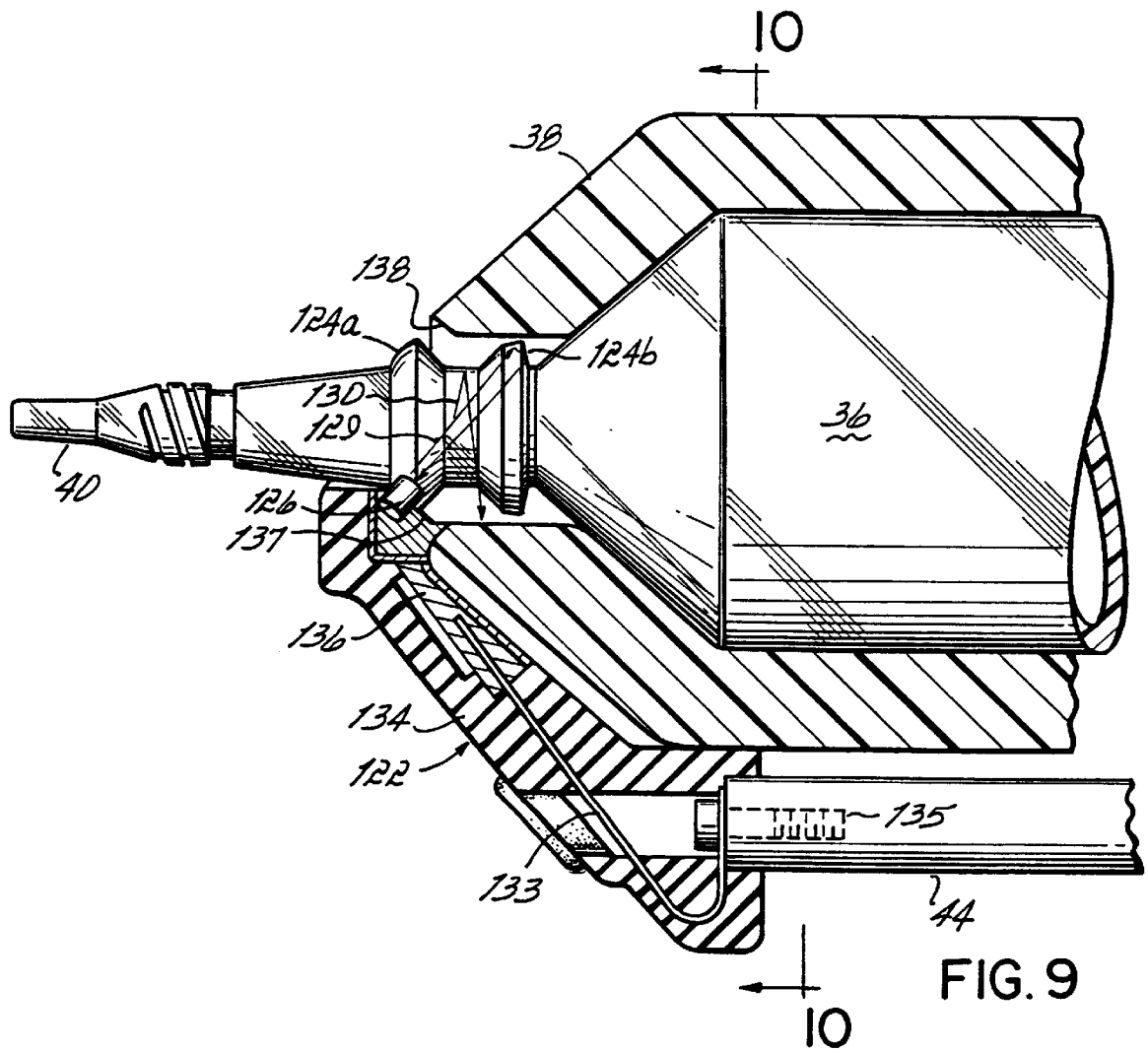
FIG. 9 is a partial cross-sectional view of a syringe mounted in the pressure jacket with the air detection module in place, showing the internal structure of the air detection module and its interaction with the structure of the syringe tip.
Figure 10:
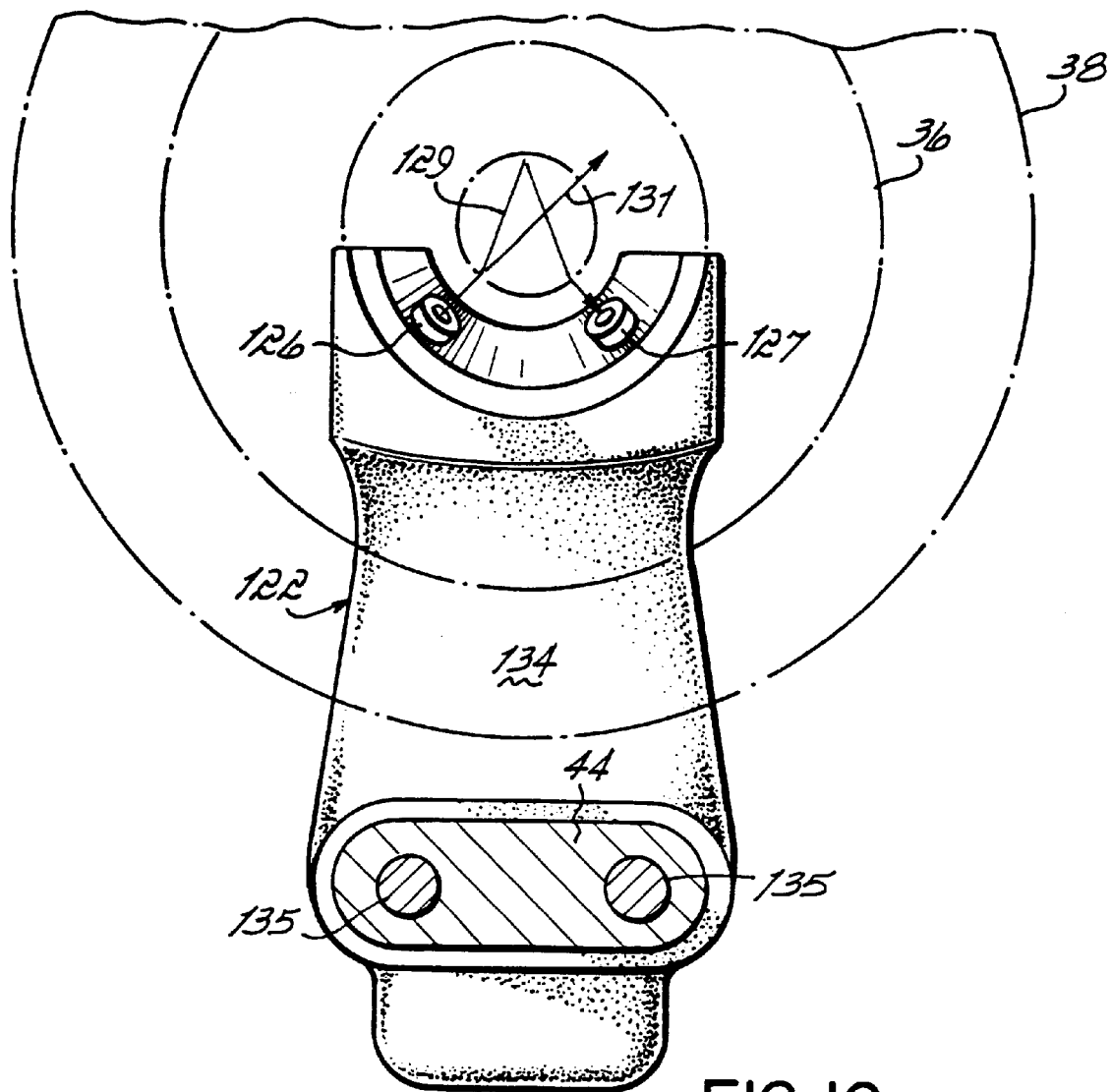
FIG. 10 is a view of the air detection module taken along lines 10—10 of FIG. 9, with the syringe and pressure jacket removed.

Referring now to FIGS. 9 and 10, the integral air detection system can be described. The air detection module 122 is mounted to the end of post 44, and is configured to wrap around the distal end of pressure jacket 38 and into contact with an outwardly projecting collar 124a surrounding the discharge neck of syringe 36. At the point of contact with collar 124a, the air detection module includes a light source 126 and light sensor 127. Light sensor 127 is a commercially available circuit, which includes sensor 127 and an oscillator which produces a trigger signal indicating when light source 126 should be stimulated to produce a light beam. The output of sensor 127 is a digital signal indicating whether the light beam is received by detector in response to triggering of the light source.

FIGS. 9 and 10 show illustrative ray traces showing the paths taken by light rays emitted from light source 126. Light source 126 includes an integral focusing lens, and collar 124a on the discharge neck of syringe 36 forms a second focussing lens. These lenses act in concert to direct light from light source 126 along path 129 toward collar 124b on the discharge neck of syringe 36. The internal shape of collar 124b forms a corner reflector, so that light impingent upon collar 124b from light source 126 is reflected toward light sensor 127.

As a result of this structure, when the neck of syringe 36 is filled with fluid, light rays emitted from light source 126 follow paths through the neck of syringe 36, which reflect and return to light sensor 127, such as path 129 illustrated in FIGS. 9 and 10. Accordingly, under such conditions, sensor 127 will produce a digital signal indicating receipt of light, which indicates the absence of air in the syringe neck. (The combined focal length of the lens in light source 126 and collar 124a, is longer than the distance travelled by light along path 129, i.e., longer than twice the distance between collar 124a and collar 124b.) However, when the neck of the syringe contains air or an air bubble, diffraction of light at air/fluid or air/syringe boundaries will cause light to deviate substantially from the path 129 illustrated in FIGS. 9 and 10. Specifically, light rays incident in the neck of syringe 36 might follow the path 130 illustrated in FIG. 9, or the path 131 illustrated in FIG. 10. In either circumstance, the presence of the air bubble prevents light from reflecting through the neck of the syringe from light source 126 to light detector 127, thus causing the light detector to produce a signal indicating failure to receive light, indicating that air is present in the neck of the syringe.

To ensure consistent, repeatable results, air detection module 122 is structured to ensure solid contact between light source 126, light sensor 127 and the surface of collar 124a on syringe 36. Specifically, the air detection module 122 has a spring-metal interior skeleton 133, which is overmolded with a soft flexible plastic 134. One end of spring metal skeleton 133 is mounted to post 44 by mounting screws 135 (which are accessible via voids in the plastic overmold 134). The opposite end of skeleton 133 supports the air detector module, which includes a hard plastic molding 136 supporting the light source 126 and light sensor 127. Molding 136 includes a beveled section 137 sized to fit into a chamfer 138 at the aperture of pressure jacket 38. The interaction of beveled section 137 and chamfer 138 ensure precise positioning of light source 126 and light sensor 127 relative to pressure jacket 38.

The neck of the syringe 36 is sized with a slight interference fit, so that collar 124a contacts and slightly deflects air detection module 122 when the syringe 36 is inserted into pressure jacket 38, flexing spring skeleton 133 and resulting in a steady application force of light source 126 and light sensor 127 against collar 124a of syringe 36. This application force ensures good communication of light from source 126 into the neck of syringe 36 and from the neck of syringe 36 into light sensor 127.

Figure 11A:
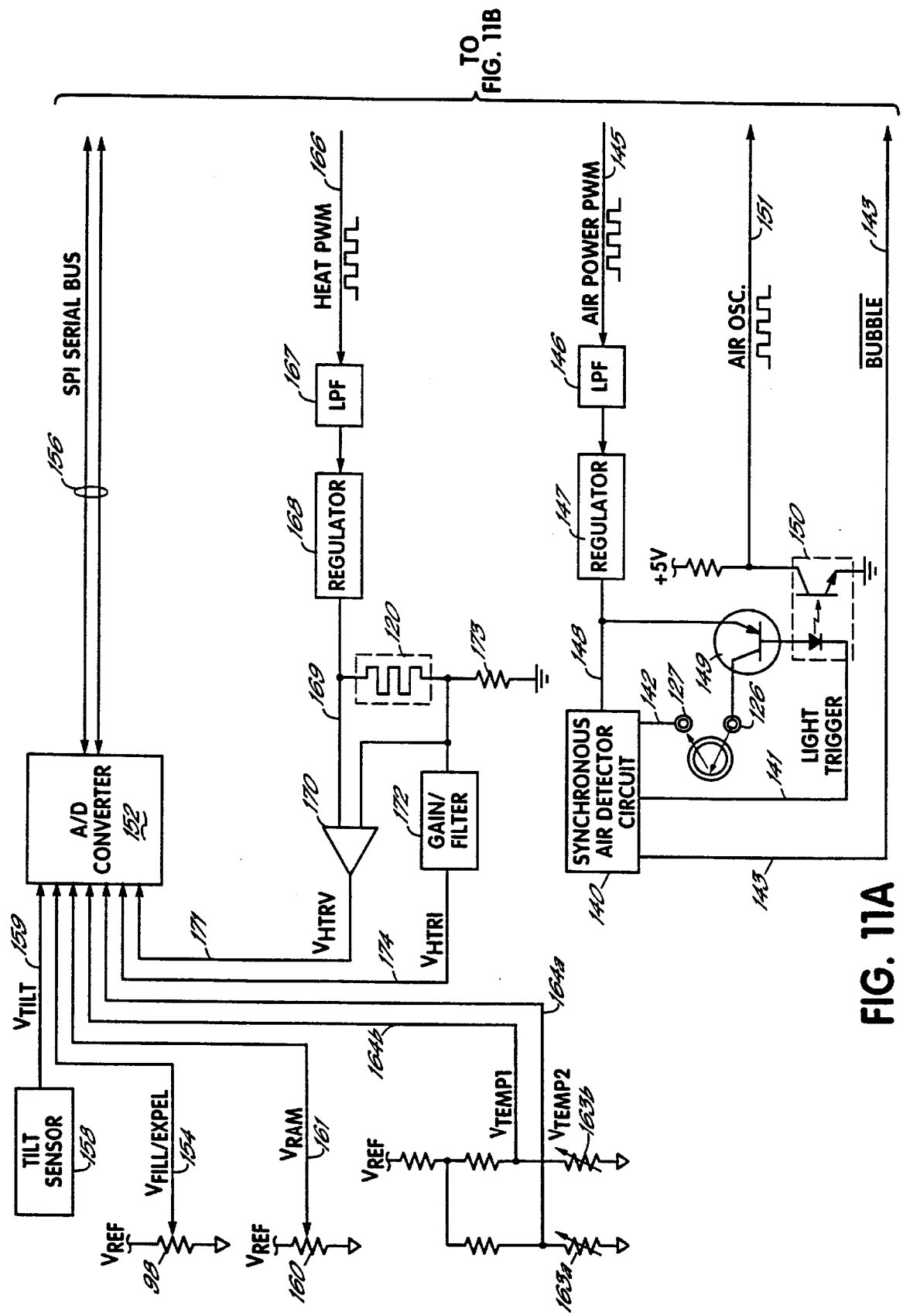
FIG. 11A is an electrical block diagram illustrating the analog circuitry in the power head, including the temperature control, air detection, and hand-operated control circuitry.

Now turning to FIG. 11A, the electrical circuit details of the air detection module, and other analog electrical systems, can be elaborated. Specifically, the air detection module incorporates therein, a commercially available synchronous detection circuit 140, which includes an internal oscillator generating trigger pulses on line 141, and, contemporaneously with each trigger pulse, detects electrical signals on line 142 indicating that light has been received at light sensor 127. So long as light is detected contemporaneously with each trigger pulse, a high level signal is produced on line 143. Due to the application to which circuit 140 is applied in accordance with the invention, the signal on line 143 indicates whether air has been detected in the neck of the syringe 36.

The control circuit of power head 22 may control the light intensity applied to the air bubble detector, to control the sensitivity of the detector. To do so, the control circuit produces a pulse width modulated (PWM) digital signal on line 145. This PWM signal is filtered by a low-pass filter circuit 146 to produce an analog control voltage, which controls an adjustable regulator 147 to produce the power signal on line 148 for circuit 140.

In response to the trigger signal on line 141, a PNP optp-transistor 149 is turned "on", causing the power signal on line 148 to energize light source 126. Thus, the voltage of the power signal on line 148 directly affects the intensity of light generated by light source 126.

So that the control circuit may monitor the air detector circuit 140 for possible failures, the trigger signal on line 141 is connected to the base of PNP opto-transistor 149 via a light emitting diode in an opto-isolator 150. Accordingly, the opto-transistor in opto-isolator 150 will turn "on" whenever the trigger signal is activated, causing a "low" level to appear on line 151. Thus, if the synchronous air detector circuit 140 is operating properly and producing periodic trigger signals, pulses will appear on line 151, which can be detected by the control circuit to verify that the oscillator in circuit 140 is operating properly.

FIG. 11A also illustrates the analog-to-digital (A/D) converter 152 incorporated into the power head control circuit for quantizing analog signals produced by various electrical elements. For example, potentiometer 98 (see FIG. 6) is connected to the shaft 48 of fill/expel lever 29. The wiper of this potentiometer is connected to a signal line 154, which carries an analog voltage indicative of the rotational position of the fill/expel lever shaft 48. The opposite ends of the potentiometer are connected to a reference voltage and to ground, so that the voltage on line 154 lies somewhere between these extremes, dependent upon the rotational position of fill/expel lever 29. Line 154 connects to A/D converter 152, and converter 152 converts the analog voltage on line 154 to a digital signal on a "SPI" serial interface bus 156, upon request from the CPU (see FIG. 11B), so that the CPU can determine the position of fill/expel lever 29 and react accordingly.

Other analog voltages are also input to A/D converter 152. Specifically, a single-chip accelerometer is configured as a tilt sensor 158, to produce an analog voltage on line 159 indicative of the angle of tilt of sensor 158. (A suitable single chip accelerometer for this purpose is available from Analog Devices of Norwood, Mass. as part no. ADXL05AH.) Sensor 158 is mounted to circuit board 55, and therefore produces an output voltage indicative of the tilt of power head 22 relative to the direction of Earth gravity. This analog tilt signal is converted and input to the CPU for use, as noted below, in controlling the display and other operational features of power head 22.

A third analog signal is produced by a linear potentiometer 160, the wiper of which is mechanically connected to the plunger drive ram 62, and moved in response to movement of the plunger drive ram. Thus, the voltage of the wiper on line 161 is an analog signal representative of the position of the ram between its rearward most and forward most positions. This signal is converted and used by the CPU to determine the position of the ram and, among other things, the syringe volume remaining.

Two additional analog signals are produced by thermistors 163A and 163b, which are series connected with bias resistors to produce voltages on lines 164a and 164b which reflect the temperature of the thermistors. The temperature measurement obtained from these thermistors is then used to control the power applied through the heater blanket to warm the fluid in the syringe 36. Specifically, the heat power applied to the syringe is varied proportion to the ambient temperature, as measured by thermistors 163a and 164a, to maintain the fluid at the target temperature, e.g., 30 degrees Celsius.

Thermistors 163a and 163b are duplicative, that is, both measure the same temperature and their measurements are compared to ensure near agreement. As a result, failure of a thermistor can be detected from disagreement between the temperature readings obtained from the thermistors, preventing loss of temperature control.

Thermistors 163a and 163b may be mounted internally to power head 22, on circuit board 55. Alternatively, thermistors 163a and 163b may be external to the housing, to ensure more accurate temperature readings, or both options may be allowed by providing internally-mounted thermistors which can be disabled if substitute externally-mounted thermistors are connected to the power head 22.

As noted above, using thermistors 163a and 163b, power head 22 controls the heat power applied to the syringe 36 through heater blanket 42. To perform this function, the CPU (see FIG. 11B) produces a pulse width modulated (PWM) control signal on line 166 which is used to control the heat power applied to the heater blanket filament 120. Specifically, the PWM signal on line 166 is low pass filtered by filter 167, producing an analog control signal which controls an adjustable regulator 168. The output of regulator 168 on line 169 is a variable voltage which is applied across heater blanket filament 120, causing heater filament 120 to produce heat.

An instrumentation amplifier 170 filters and conditions the voltage across filament 120 to produce an analog output signal on line 171 which is proportional to the voltage applied to the heater blanket filament 120.

A sense resistor 173 is series connected with heater filament 120, so that the current in heater filament 120 passes through sense resistor 173, producing a voltage on sense resistor proportional to the current flowing through heater filament 120. Sense resistor has a resistance substantially smaller than that of heater filament 120, so that the small voltage drop across sense resistor 173 is not a substantial percentage of the voltage drop across heater filament 120.

The voltage drop across sense resistor 173 is amplified and filtered by a gain/filter circuit 172, producing an analog voltage on line 174 which is proportional to the current flowing through heater filament 120.

Lines 171 and 174 are connected to A/D converter 152, and the voltages on lines 171 and 174 are converted thereby to digital signals which can be read by the CPU. Accordingly, the CPU can determine the current and voltage drop across heater filament 120, and use these values to determine the heat output of heater filament 120. This permits the CPU to perform closed-loop control of the heater blanket heat output, as discussed below in connection FIG. 12.

Figure 11B:
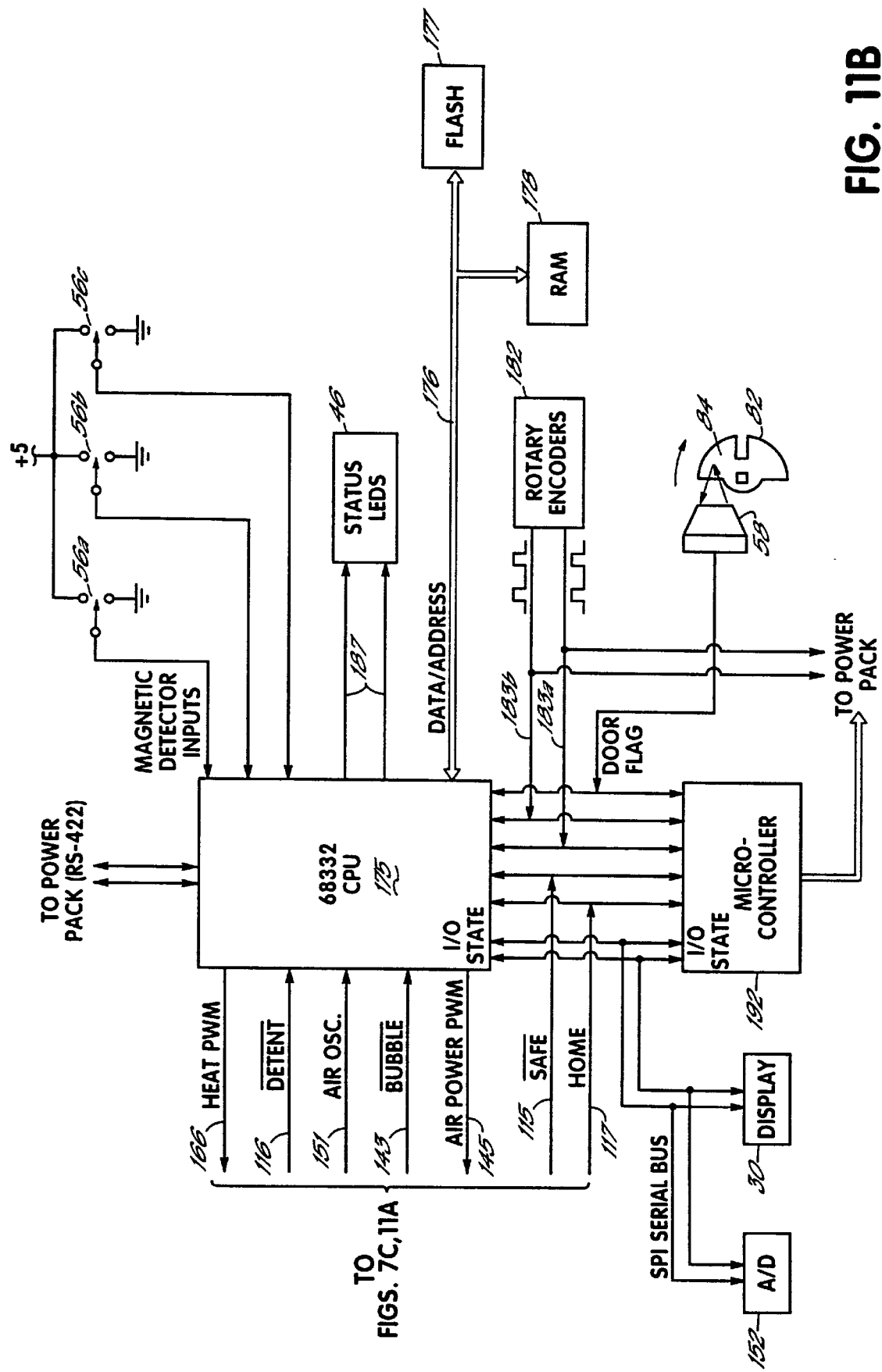
FIG. 11B is an electrical block diagram of the digital control circuitry in the power head, including the central processing unit, monitor microcontroller, digital status, control and interface connections.

Referring now to FIG. 11B, the connections to the CPU of the power head 22 can be understood. The CPU 175, which may be a 68332 microprocessor, available from Motorola, controls data and address busses 176 connecting CPU 175 to random access memory (RAM) 178 and a flash memory 177. CPU 175 also controls an SPI serial interface bus 156 for communicating with A/D converter 152, display 30 and a monitor microcontroller 192. CPU 175 further includes an RS-422 serial interface 179 connecting CPU 175 to a CPU in the power pack (see FIG. 11C).

CPU 175 includes a number of digital data input lines for monitoring operation of power head 22. Specifically, CPU 175 receives the detent signal on line 116, safe signal on line 115 and home signal on line 117, enabling CPU to receive input on the state of operation of the hand-operated movement lever as discussed above. CPU 175 also receives the bubble signal on line 143 from which CPU 175 may detect air in the syringe neck and take appropriate action, and in addition, CPU 175 receives the bubble detection oscillator signal on line 151, which can be used as noted above to confirm proper operation of the oscillator in the air detection module 122. Further, CPU 175 receives the output of flag sensor 58, from which CPU 175 may determine whether the face plate is securely locked to the housing of power head 22. Furthermore, CPU 175 receives digital signals from the three magnetic detectors 56a, 56b and 56c indicative of which of several possible face plates are mounted to power head 22, allowing CPU 175 to adjust its operation accordingly.

CPU 175 also receives digital input signals from parallel rotary encoders 182, which produce pulse signals on lines 183a and 183b indicative of rotation of the plunger drive train. These pulses are used by CPU 175 to confirm movement of the plunger drive ram. Lines 183a and 183b are also connected to the power pack (see FIG. 11C) so that the power pack CPU may perform closed loop control of plunger movement by counting encoder pulses and comparing the rate of receipt of encoder pulses to a desired rate. A closed loop control is disclosed in U.S. Pat. No. 4,812,724, which is incorporated by reference herein in its entirety.

CPU 175 also produces multiple digital control signals, including those noted above, i.e., the air bubble detector power PWM signal on line 145, and the heater blanket power PWM signal on line 166, both being pulse-width modulated by CPU 175 to produce desired power levels. CPU 175 further produces output signals on lines 187 for illuminating light emitting diodes in lamp 46 (FIG. 2) which indicate the status of operation of the injector. Additional output signals on SPI serial bus lines 156 control the display 30.

CPU 175 uses the above-noted inputs and outputs to perform primary control of power head 22 under control of software resident in CPU 175 or read from RAM 178. As noted above, CPU 175 is also connected, through SPI serial bus 156, to a microcontroller 192 which serves as a monitor, for monitoring operation of CPU 175 to ensure the absence of software or hardware failures. (Microcontroller may be a single-chip microcontroller available from Microchip Technologies as part no. PIC16C63.) Monitor microcontroller 192 performs this function by receiving, through bus 156, an indication of the current operational state of CPU 175.

Specifically, CPU 175 indicates, through bus 156, the operating state of CPU 175, i.e., whether CPU 175 is requesting movement of the plunger or not, and whether the motion is being requested in response to hand-operated or automatic (programmed) control, and potentially other specific information such as the rate of movement that is being requested. Monitor microcontroller 192 reads this state information from lines 156, and compares this information to crucial digital input signals from the power head 22, to ensure consistency therebetween.

For example, microcontroller 192 receives the safe signal on line 115 and home signal on line 117. If these signals indicate that the hand-operated control is in the home position, then CPU 175 should not be generating movement under hand-operated control. If a spring has failed (as indicated by the signal on line 115), this should be reflected in the state of the CPU 175. Therefore, under these conditions, microcontroller 192 reads the state information from bus 156 to ensure that CPU 175 is not acting inconsistently with the signals from the hand-operated control.

As a second example, microcontroller 192 receives the output signals from rotary encoders 182 on lines 183a and 183b. Microcontroller 192 checks these signals to determine whether the plunger drive ram is moving, to ensure the drive ram is moving only when the state of CPU 175 indicates that the drive ram should be moving, and not otherwise. Furthermore, in this connection it should be noted that microcontroller 192 receives the door flag signal from door flag sensor 58. If this signal indicates that the door of power head 22 is other than in the locked position, CPU 175 should not be requesting movement of the plunger drive ram, and microcontroller 192 confirms this by checking for the absence of pulses from encoders 182.

Referring now to FIG. 11C, the interaction of the power head 22, power pack 26 and console 24 can be further understood. Specifically, each of power head 22, power pack 26 and console 24 contains a CPU 175, 192 and 194, respectively. These CPUs interact through external interfaces to perform control of the injector. For example, the plunger drive ram can be controlled through the lever 29 on power head 22 (as discussed above), or can be automatically controlled by an operator entering programs for injections using touch screen 32 of console 24 (using CPU 194), and then enabling the programmed injection. The injection parameters such as motor speed and injection volumes will then be produced by console CPU 194, which communicates with power pack CPU 192 to cause these programmed actions to take place. Furthermore, an automatic injection may be enabled using the touch screen 32, or an injection may be started using a hand switch or OEM remote trigger connected to power pack 26. In either case, the appropriate one of CPUs 192 and 194 generates an enabling signal to initiate the automatic injection.

As noted above, the power head CPU 175 is associated with a monitor microcontroller 192 for monitoring the state of CPU 175 to ensure its actions are consistent with input signals from power head 22. Similarly, CPUs 192 and 194 are also associated with monitor microcontrollers 196 and 198, respectively, which monitor the actions of the associated CPUs 196 and 198 to ensure consistent, error free behavior.

Monitor microcontrollers 192, 196 and 198 communicate with each other in a manner which parallels the communication of CPUs 175, 192 and 194. Specifically, the three monitor microcontrollers exchange state information received from their associated CPUs to ensure that the three CPUs are in similar states of operation, e.g., hand-operated movement, automatic movement, no movement, etc. Furthermore, each of the microcontrollers receives external input signals to ensure that state transitions which should occur are, in fact, occurring. Thus, microcontroller 196 receives the hand or OEM trigger signals so that microcontroller 196 can determine when an automatic injection has been triggered. Microcontroller 198 receives input signals from touch screen 32 so it, too, can determine when an automatic injection has been triggered. Other monitoring functions can be performed, as desired to ensure correct and consistent operation of CPUs 175, 192 and 194.

As noted above, power head CPU 175 delivers a control signal to power pack 26, requesting a ram movement. Power pack 26 contains the motor servo control circuitry for producing an appropriate power signal on line 200 to drive motor 63, and to perform closed loop control of motor movements in response to encoder pulses on lines 183.

In error conditions, the monitor microcontrollers can discontinue power flow to motor 63 through a hardware disable, represented by switch 202 in series with power line 200, thereby ceasing any movement of the plunger drive. This hardware disable ensures that the monitor microcontrollers can prevent erroneous injection of fluid under error conditions.

Figure 12:
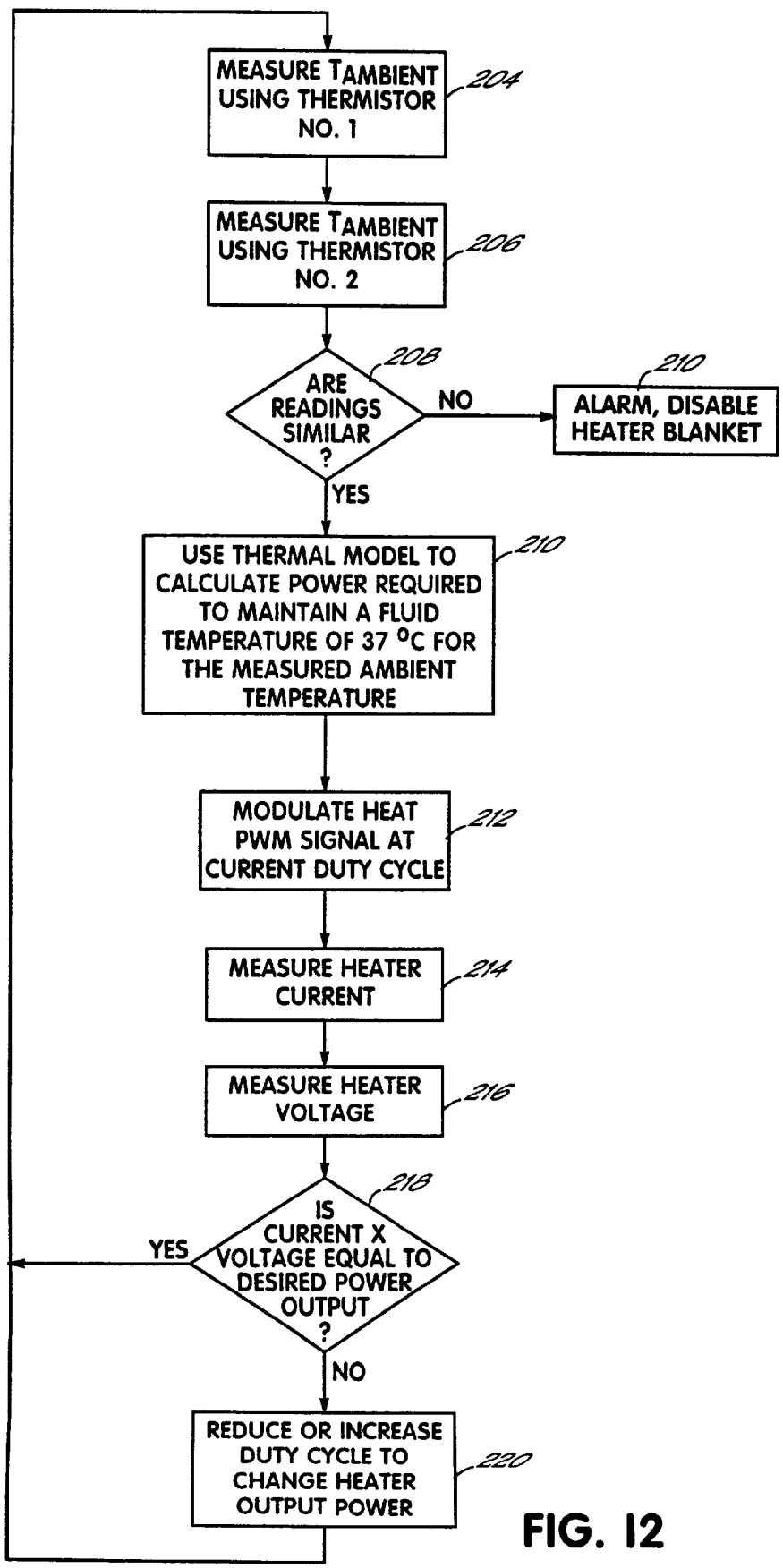
FIG. 12 illustrates the heater blanket temperature control methodology used by the CPU of the power head.

Referring now to FIG. 12, the heater blanket control functions performed in power head CPU 175 may be explained. To perform heater blanket control, CPU 175 initially measures the ambient temperature using the first and second thermistors 163a and 163b (steps 204 and 206). (As part of these steps, CPU 175 may reference stored compensation tables for converting thermistor voltages to corresponding temperatures.) CPU 175 then determines whether these temperature readings are consistent with each other (step 208). If not, this indicates a fault in a thermistor, and an alarm is generated, and the heater blanket is disabled (step 210).

If the thermistor temperature readings are similar, then CPU 175 proceeds to determine a desired heater blanket power output level $P_{OUT}$ (step 210), based on the measured ambient temperature $T_{AMBIENT}$. A thermal model is used to calculate the power required to maintain the fluid temperature at 37° C. with the measured ambient temperature. The power will vary according to this model over the range of ambient temperatures from 0° C. to 32° C. Above an ambient temperature of 32° C., the heater blanket is shut off to avoid over heating the fluid. Below an ambient temperature of 0° C., the power produced by the heater blanket is limited to 8 Watts to avoid overheating the heater filament 120 in the heater blanket. One simplified thermal model would be a linear model, in which the output power is determined by the formula $P_{OUT}=B-AT_{AMBIENT}$, where B and A are empirically computed offset and gain factors, and $P_{OUT}$ is limited to eight Watts. Other models might also be used, particularly non-linear models.

To produce this desired output heat power, CPU 175 produces a PWM signal on line 166 (FIGS. 11A and 11B) at a duty cycle (step 212). An initial duty cycle is chosen to begin warming the fluid in the syringe.

As this PWM duty cycle is produced, CPU 175 reads, from lines 171 and 174 (through A/D converter 152), the analog voltages indicating the voltage and current applied to heater filament 120 (steps 214 and 216). These values are multiplied to determine the actual power being output from the heater blanket, and this power is compared (step 218) to the desired output power computed earlier. If the current output power is approximately equal to the desired power, then the current PWM duty cycle is correct, and CPU 175 will return to step 204 to re-measure the ambient temperature to continue controlling the heater output power. If, however, the heater output power is either too large or too small, CPU 175 will proceed first to step 220, and adjust the PWM duty cycle to change the heater output power as needed (by reducing the duty cycle if too much power is being produced, or by increasing the duty cycle if too little power is being produced). Thereafter, CPU 175 will return to step 204 to re-measure ambient temperature to continue controlling the heater output power.

This temperature control methodology ensures accurate control of the temperature of the fluid in syringe 36, compensating for temperature variations which can be caused by variations in ambient temperature, thus reducing the likelihood of thermal shock in the subject caused by injection of fluid which is not at the desired temperature.

Figure 13A:
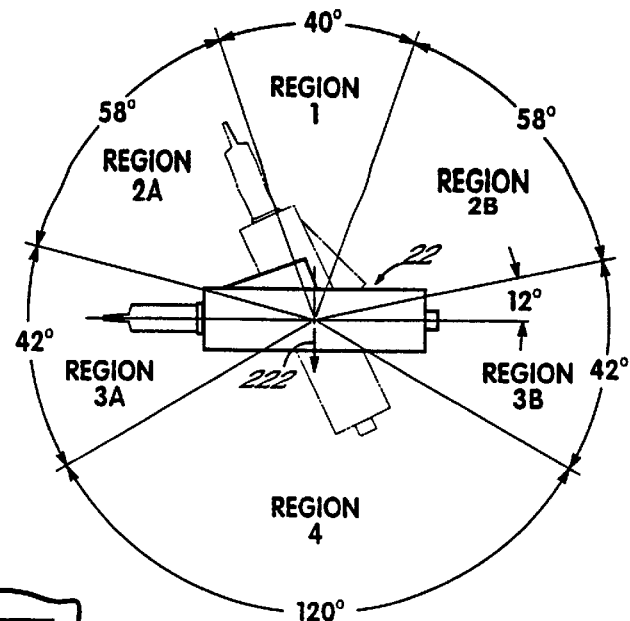
FIG. 13A illustrates the ranges of tilt angle established by software in the power head microprocessor to control operations of the injector.
Figure 13B:
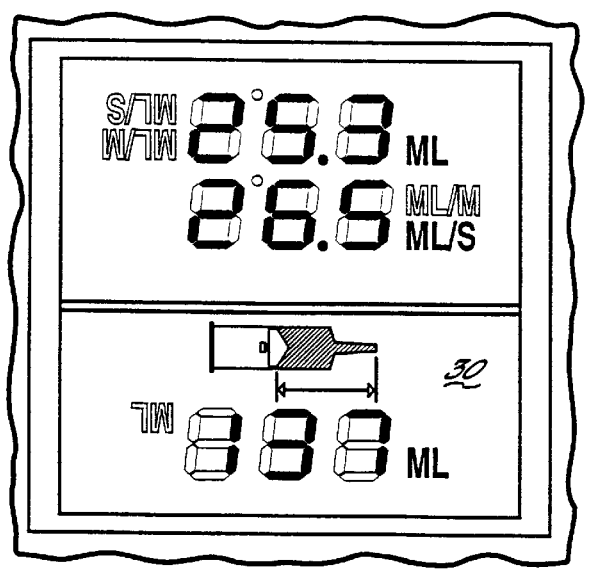
FIG. 13B illustrates the elements in the display on the power head, and a typical display output as it would appear when the power head is at a first tilt angle.
Figure 13C:
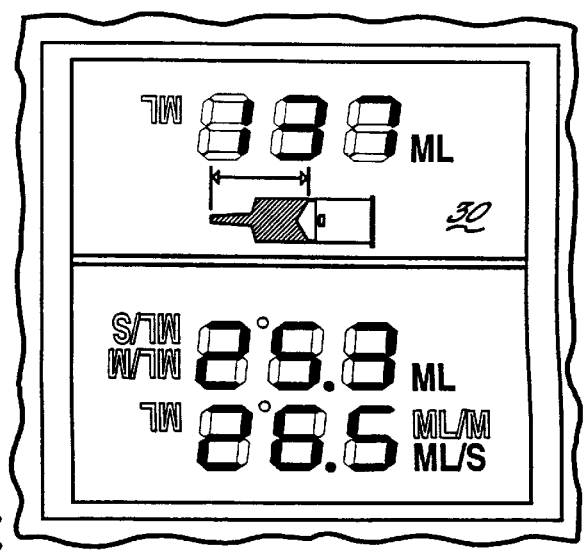
FIG. 13C illustrates the display output of the same information as FIG. 13B, as it would appear when the power head is at a second tilt angle.

Now referring to FIGS. 13A–13C, the operation of the invertible display can be understood. Specifically, as noted above, CPU 175 receives a signal from tilt sensor 158 indicative of the angle of power head 22 relative to Earth gravity. CPU 175 repeatedly samples this signal, and determines the angle of power head 22 with respect Earth gravity (direction 222). All possible angles of rotation are divided into six regions of operation, illustrated in FIG. 13A.

Region 1 is the "fill" region; it is the angle at which the power head 22 should be placed for filling the syringe. When the power head 22 is at an angle within region 1, or within regions 2a or 2b which are adjacent thereto, the power head will permit hand-operated motion of the plunger drive ram in either the forward or reverse direction, allowing the operator to fill the syringe and remove air from the syringe after initial filling. A wide range of movement speeds can be generated with the hand-operated movement control, permitting rapid filling of the syringe. While the power head 22 is in regions 1, 2a or 2b, however, programmed injections are inhibited; thus, the operator cannot initiate injection of a subject according to a pre-programmed injection protocol while the power head 22 is in an upright position. This minimizes the likelihood of accidental injection of air into the subject.

Region 4 is the "inject" region. When the power head 22 is tilted in this region, programmed injections can be initiated. Furthermore, the hand-operated movement lever 29 can be used to move the plunger drive ram in either the forward or reverse directions; however, the range of movement speeds that can be generated with the hand-operated movement control is substantially narrowed as compared to those available in regions 1, 2a or 2b. This permits fine-tuned control of fluid injection (or withdrawal of blood, e.g., to check patency of the catheter) using the hand-operated movement control.

Regions 3a and 3b can also be used to perform injection. It may be necessary to use power head tilt angles in these regions if an obese patient or other obstacle prevents the operator from rotating the power head 22 to a fully downward position in region 4. However, since operation in regions 3a and 3b is not advisable, due to the chance that air might be injected into the subject, the operator is prevented from injecting in these regions until a software override is entered via the console touch screen 32. Until this override is entered, the display 30 flashes and the injector will not perform programmed injections. Once the software override has been entered, the display will cease flashing and programmed injections can be performed. Also, as in region 4, the hand-operated movement lever 19 can be used to move the plunger drive ram in either the forward or reverse directions, with a narrow range of movement speeds, permitting fine-tuned control of fluid injection (or withdrawal) using the hand-operated movement control.

The various angular regions noted above, are also associated with display orientations. Specifically, as can be seen in FIGS. 13B and 13C, the display 30 of the power head 22 is a segmented display, including segments which can be illuminated to provide injection information such as volume injected, volume remaining, and current flow rate. These segments are arranged so the noted information can be displayed in either a first (see FIG. 13B) or second (see FIG. 13C) orientation.

CPU 175 in the power head 22 drives display 30 to produce the display orientation, using the display elements in the manner illustrated in FIG. 13C, when the power head angle is in regions 1, 2a or 2b. Otherwise, in regions 3a, 3b or 4, CPU 175 drives display 30 to produce the display shown in FIG. 13B. As a result, the information appearing on the display 30 is always upright from the perspective of the operator, facilitating use of the display. (There is a hysteresis included in the detection of the boundaries between the various regions shown in FIG. 13A, to prevent unintended toggling between regions.)

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, the control circuit could produce an injection pressure or fill vacuum proportional to the extent of angular displacement of control lever 29 away from the home position, rather than a velocity proportional to the extent of rotation. Air bubble detection may be performed by an ultrasonic source and ultrasonic detector coupled to the neck of the syringe, in which case air can be detected from the large attenuation of sound in air as compared to fluid. The air bubble detector might be mounted on locations on the syringe other than on the neck. Also, the air bubble detector may be used in connection with the power head control circuitry to perform an automatic syringe-filling function, e.g., to detect when air has been evacuated from the syringe after filling. Also, a fully pixilated display might be used on the power head 22, and controlled by the power head CPU to produce various orientations of display, not limited to upright and inverted display orientations. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An injector for injecting fluids from a syringe into an animal subject, having a hand-operated movement control for controlling movements of said injector, said injector comprising:

a plunger drive ram, a motor for moving said plunger drive ram, a syringe mounting for attachment to a syringe to position a syringe relative to said injector to permit said plunger drive ram to engage and move a plunger into or out of said syringe, a control circuit controlling said motor to move said ram and plunger to inject fluid from said syringe, and a hand-operated movement control comprising a lever movable between a home position and forward and reverse positions, said control circuit responding to forward movement of said lever by moving said plunger drive ram into said syringe to expel fluid from the syringe at a rate related to the amount of forward movement of said lever from said home position, said control circuit responding to reverse movement of said lever by moving said plunger drive ram out of said syringe to draw fluid into the syringe at a rate related to the amount of reverse movement of said lever from said home position.

2. The injector of claim 1 wherein said lever is mounted in said injector on a pivot shaft, and further comprising return springs positioned on opposite sides of said lever such that rotation of said lever away from said home position bends said return springs.

3. The injector of claim 2 further comprising a rotational detector attached to said pivot shaft for rotation with said lever to detect an angle of rotation of said lever to produce a rotation angle signal, wherein said control circuit responds to said rotation angle signal by moving said plunger drive ram at a speed related to said rotation angle signal.

4. The injector of claim 3 wherein said control signal moves said plunger drive ram at a speed proportionate to said angle of rotation of said lever.

5. The injector of claim 3 wherein said rotational detector is a rotary potentiomneter.

6. The injector of claim 2 further comprising a rotational detector attached to said pivot shaft for rotation with said lever to detect an angle of rotation of said lever to produce a rotation angle signal, wherein said control circuit responds to said rotation angle signal by moving said plunger drive ram so as to generate an injection pressure related to said rotation angle signal.

7. The injector of claim 2 wherein said return springs and said lever are electrical contacts, and further comprising a safety circuit generating a safety control signal indicating whether there is electrical contact between said return springs and said lever, said control circuit responding to said safety control signal, whereby the failure of a return spring is electrically detectable by said control circuit.

8. The injector of claim 2 further comprising a detent spring positioned relative to said lever to engage said lever upon rotation of said lever into a position which is more than a predetermined angle from said home position, said detent spring producing additional resistive torque opposing rotation of said lever away from said home position beyond said predetermined angle.

9. The injector of claim 8 wherein said detent spring is positioned relative to said lever to engage said lever upon rotation of said lever to a reverse position.

10. The injector of claim 9 wherein said detent spring and said lever are electrical contacts, further comprising a detent circuit generating a detent signal indicating whether there is electrical contact between said detent spring and said lever, said control circuit responding to said detent signal by moving said plunger drive ram out of said syringe to draw fluid into said syringe at a predetermined recommended maximum speed.

11. A method of controlling an injector for injecting fluid from a syringe into an animal subject, using a hand-operated movement control for controlling movements of said injector, the method comprising:

providing an injector having a plunger drive ram, a motor for moving said plunger drive ram, a syringe mounting for attachment to a syringe to position a syringe relative to said injector to permit said plunger drive ram to engage and move a plunger into or out of said syringe, a control circuit controlling said motor to move said ram and plunger to inject fluid from said syringe, and a hand-operated movement control comprising a lever movable between a home position and forward and reverse positions, responding to forward movement of said lever by moving said plunger drive ram into said syringe to expel fluid from the syringe at a rate related to the amount of forward movement of said lever from said home position, and responding to reverse movement of said lever by moving said plunger drive ram out of said syringe to draw fluid into the syringe at a rate related to the amount of reverse movement of said lever from said home position.

* * * * *